(12) United States Patent
Meaney et al.

(10) Patent No.: US 6,879,853 B2
(45) Date of Patent: *Apr. 12, 2005

(54) METHOD AND APPARATUS FOR MAGNETIC RESONANCE ARTERIOGRAPHY USING CONTRAST AGENTS

(76) Inventors: James F. M. Meaney, CT/MRI Department, Claredon Wing, Belmont Grove, Leeds General Infirmary, Leeds LS29NS (GB); Martin R. Prince, 403 Riverview Dr., Ann Arbor, MI (US) 48104

( * ) Notice: Subject to any disclaimer, the term of this patent is extended or adjusted under 35 U.S.C. 154(b) by 208 days.

This patent is subject to a terminal disclaimer.

(21) Appl. No.: 10/350,487

(22) Filed: Jan. 24, 2003

(65) Prior Publication Data

US 2003/0135111 A1 Jul. 17, 2003

Related U.S. Application Data

(63) Continuation of application No. 10/032,860, filed on Oct. 23, 2001, now Pat. No. 6,564,085, which is a continuation of application No. 09/309,311, filed on May 11, 1999, now Pat. No. 6,311,085, which is a continuation of application No. 08/944,426, filed on Oct. 6, 1997, now Pat. No. 5,924,987.

(51) Int. Cl.[7] .............................................. A61B 5/055
(52) U.S. Cl. ..................................... 600/420; 324/309
(58) Field of Search ................................ 600/410, 415, 600/419, 420; 324/306, 307, 309

(56) References Cited

U.S. PATENT DOCUMENTS

| | | |
|---|---|---|
| 3,973,554 A | 8/1976 | Tipton |
| 4,006,736 A | 2/1977 | Kranys et al. |
| 4,202,333 A | 5/1980 | Thill et al. |

(Continued)

OTHER PUBLICATIONS

"Frequency Dependence of Tissue Relaxation Times", Bottomley, Relaxation Relaxometry, 1987, pp. 1075–1086.
"Magnetic Resonance Imaging", Stark et al., vol. 2, second edition, pp. 1518–1520 and 1854–1859 (Chpt. 52), 1992.
"Magnetic Resonance Angiography of the Renal and Visceral Arteries", Kaufman, et al., Magnetic Resonance Angiography: A Practical Approach, McGraw–Hill, Incorporated, 1995, Chapter 12, pp. 161–170.
"Magnetic Resonance Angiography of the Thoracic Aorta", Prince, et al., Magnetic Resonance Angiography: A Practical Approach, McGraw–Hill, Incorporated, 1995, Chapter 10, pp. 131–138.

(Continued)

Primary Examiner—Ruth S. Smith
(74) Attorney, Agent, or Firm—Neil A. Steinberg

(57) ABSTRACT

The present invention is a technique of, and system for, imaging vascular anatomy over distance considerably greater than the maximum practical field of view of a magnetic resonance imaging system while using substantially one contrast agent injection. The technique and system of the present invention acquires image data of a plurality of image volumes which are representative of different portions of the patient's body. The image data of each image volume includes image data which is representative of the center of k-space. The acquisition of image data which is representative of the center of k-space is correlated with a concentration of contrast agent in the artery(ies) residing in the image volume. This provides preferential enhancement of arteries relative to adjacent veins and background tissue for each acquisition, wherein each acquisition is representative of a different portion of the arterial system (e.g., abdominal aorta, femoral, popliteal, and tibial arteries).

30 Claims, 12 Drawing Sheets

U.S. PATENT DOCUMENTS

| | | |
|---|---|---|
| 4,298,000 A | 11/1981 | Thill et al. |
| 4,430,079 A | 2/1984 | Thill et al. |
| 4,585,008 A | 4/1986 | Jarkewicz |
| 4,585,941 A | 4/1986 | Bergner |
| 4,597,754 A | 7/1986 | Thill et al. |
| 4,718,424 A | 1/1988 | Nishimura |
| 4,770,182 A | 9/1988 | Damadian et al. |
| 4,770,183 A | 9/1988 | Groman et al. |
| 4,777,957 A | 10/1988 | Wehrli et al. |
| 4,822,594 A | 4/1989 | Gibby |
| 4,826,673 A | 5/1989 | Dean et al. |
| 4,865,043 A | 9/1989 | Shimoni |
| 4,877,599 A | 10/1989 | Lees |
| 4,880,008 A | 11/1989 | Lauffer |
| 4,915,111 A | 4/1990 | Sano et al. |
| 5,010,191 A | 4/1991 | Engelstad et al. |
| 5,011,686 A | 4/1991 | Pang |
| 5,034,694 A | 7/1991 | Sattin et al. |
| 5,055,288 A | 10/1991 | Lewis et al. |
| 5,078,986 A | 1/1992 | Bosworth et al. |
| 5,087,439 A | 2/1992 | Quay |
| 5,111,492 A | 5/1992 | Klausz |
| 5,141,740 A | 8/1992 | Rajagopalan et al. |
| 5,167,232 A | 12/1992 | Parker et al. |
| 5,190,744 A | 3/1993 | Rocklage et al. |
| 5,204,629 A | 4/1993 | Ueyama |
| 5,236,417 A | 8/1993 | Wallis |
| 5,243,284 A | 9/1993 | Noll |
| 5,260,050 A | 11/1993 | Ranney |
| 5,287,273 A | 2/1994 | Kupfer et al. |
| 5,301,672 A | 4/1994 | Kalender |
| 5,305,751 A | 4/1994 | Chopp et al. |
| 5,315,997 A | 5/1994 | Widder et al. |
| 5,341,099 A | 8/1994 | Suzuki |
| 5,398,686 A | 3/1995 | Inoue et al. |
| 5,417,213 A | 5/1995 | Prince |
| 5,423,315 A | 6/1995 | Margosian et al. |
| 5,451,211 A | 9/1995 | Neer et al. |
| 5,472,403 A | 12/1995 | Cornacchia et al. |
| 5,494,036 A | 2/1996 | Uber, III et al. |
| 5,515,851 A | 5/1996 | Goldstein |
| 5,515,863 A | 5/1996 | Damadian |
| 5,522,390 A | 6/1996 | Tuithof et al. |
| 5,553,619 A | 9/1996 | Prince |
| 5,579,767 A | 12/1996 | Prince |
| 5,590,654 A | 1/1997 | Prince |
| 5,684,398 A | 11/1997 | Takiguchi et al. |
| 5,692,508 A | 12/1997 | Simonetti et al. |
| 5,746,208 A | 5/1998 | Prince |
| 5,762,065 A | 6/1998 | Prince |
| 5,768,336 A | 6/1998 | Khutoryansky et al. |
| 5,792,056 A | 8/1998 | Prince |
| 5,799,649 A | 9/1998 | Prince |
| 5,808,468 A | 9/1998 | Bis et al. |
| 5,833,607 A | 11/1998 | Chou et al. |
| 5,873,825 A | 2/1999 | Mistretta et al. |
| 5,924,987 A | 7/1999 | Meaney et al. |
| 5,928,148 A | 7/1999 | Wang et al. |
| 6,167,293 A | 12/2000 | Chenevert et al. |
| 6,230,041 B1 | 5/2001 | Prince |
| 6,240,311 B1 | 5/2001 | Prince |
| 6,243,600 B1 | 6/2001 | Prince |
| 6,278,892 B1 | 8/2001 | Prince |
| 6,311,085 B1 | 10/2001 | Meaney et al. |
| 6,564,085 B2 * | 5/2003 | Meaney et al. ............ 600/415 |
| 6,754,521 B2 * | 6/2004 | Prince ....................... 600/420 |

OTHER PUBLICATIONS

Dixon, "Simple Proton Spectroscopic Imaging", Radiology, Nov. 25, 1984, pp. 189–194.

"Breath–Held 3D Gadolimium–Enhanced Renal Artery MRA", Prince et al., Proceedings of SMR, Aug. 1995.

"Measuring Signal Intensity Curves in Both Blood and Tissue During Contrast Agent Administration using a Novel Rapid Interleaved Method", Taylor et al., SMRM Aug. 1993, p. 474.

"Clinical Evaluation of Pulmonary 3D Time–of–Flight MRA with Breath–Holding Using a Contrast Media", Isoda et al., Journal Computer Assisted Tomography, 19(6):911–919, Nov.–Dec. 1995.

"Gd–DTPA Enhanced Multi–slab 3D MR Angiography of Aorto–iliac Arteries", Amanuma et al., SMRM, Aug. 1993, p. 524.

"Three–dimensional MR Angiography (3D–MRA) of Aortic Diseases with Bolus Administration of Contrast Media in a Single Breath–hold", Togami et al., SMRM, Aug. 1994, p. 969.

"Dynamic Three–dimensional Imaging with Partial K–Space Sampling: Initial Application for Gadolinium–enhanced Rate Characterization of Breast Lesions", Chenevert et al., Radiology, vol. 196, No. 1, 1995, p. 135–142.

"Clinical application of pulmonary 3 dimensional time–of–flight MR angiography with breath–holding using a contrast medium", Isoda, et al., Society of Magnetic Resonance in Medicine, 11th Annual Scientific Meeting, Aug. 8–14, 1992, Berlin, Germany, Works in Progress, p. 3119, XP002111479.

"The arterial concentration of Gd–DTPA can be monitored non–invasively", Soodergaard, et al., Society of Magnetic Resonance in Medicine, 11th Annual Scientific Meeting, Aug. 8–14, 1992, Berlin, Germany, Book of Abstracts, v.1, p. 1120, XP002111480.

"Fast–scan magnetic resonance: Principles and applications", Wehrli, Magnetic Resonance Quarterly, v.6, No. 3, 1990, p. 165–236, XP002111477.

A Rapid Interleaved Method for Measuring Signal Intensity Curves in both Blood and Tissue during Contrast Agent Administration, Taylor et al., Magnetic Resonance in Medicine, 30, 1993, pp. 744–749.

"Cerebrovascular Magnetic Resonance Angiography", Wesbey et al., J. Vascular Surgery 1992, vol. 16, No. 4, pp. 619–632.

"Volume MR Angiography: Methods to Achieve Very Short Echo Times", Schmalbrock et al., Radiology 1990, vol. 175, pp. 861–865.

"Three Dimension (Volume) Gradient–Echo Imaging of the Carotid Bifurcation: Preliminary Clinical Experience", Masaryk et al., Radiology 1989, vol. 171, pp. 801–806.

"Gadolinium–enhanced Magnitude Contrast MR Angiography of Popliteal and Tibial Arteries", Lossef et al., Radiology 1989, vol. 184, pp. 349–355.

"Intracranial Circulation: Preliminary Clinical Results with Three–Dimensional (Volume) MR Angiography", Masaryk et al., Radiology 1989, vol. 171, pp. 793–799.

"Abdominal Aorta and Renal Artery Stenosis: Evaluation with MR Angiography", Kim, et al.,Radiology, vol. 174, pp. 727–731, Mar. 1990.

"Intracranial Vascular Lesions: Optimization and Clinical Evaluation of Three–Dimensional Time–of–Flight MR Angiography", Marchal, et al., Radiology, vol. 175, pp. 443–448, May 1990.

"Normal Venous Anatomy of the Brain: Demonstration with Gadopentatate Dimeglumine in Enhanced 3–D MR Angiography", Chakeres, et al., AJR, vol. 156, pp. 161–172, Jan. 1991.

"Three–dimensional Time–of–Flight MR Angiography: Applications in the Abdomen and Thorax", Lewin, et al., Radiology, vol. 179, No. 1, pp. 261–264, Apr. 1991.

"Safety of Gadolinium–DPTA: Extended Clinical Experience", Niendorf, et al., SMRM Workshop on Contrast Enhanced Magnetic Resonance, May 23–25, 1991.

"Fast Time–of–Flight MR Angiography with Improved Background Suppression", Edelman, et al, Radiology, vol. 179, pp. 867–870, Jun. 1991.

"Assessment of Carotid Artery Stenosis by MR Angiography: Comparison with X–ray Angiography and Color Coded Doppler Ultrasound", Anderson, et al., AJNR, vol. 13, pp. 989–1003, May/Jun. 1992.

"Gadolinium–enhanced High–Resolution MR Angiography with Adaptive Vessel Tracking: Preliminary Result in the Intercranial Circulation", Lin, et al, JMRI, vol. 2, pp. 277–284, May/Jun. 1992.

"A Perspective on K–Space", Mezrich, Radiology 1995 (Annual Meeting, Nov.26–Dec. 1, 1995); vol. 195, No. 2, pp. 297–315.

"Experience with High–Dose Gadolinium MR Imaging in the Evaluation of Brain Metastases", Yuh, et al., AJNR, vol. 13, pp. 335–345, Jan./Feb. 1992.

"Abdominal Aortography with Dynamic High–Dose Gadopentetate Dimeglumine", Prince, SMRM 12th Annual Meeting, Aug., 1993.

"Dynamic Gadolinium–Enhanced Three–dimensional Abdominal MR Arteriography", Prince et al.,JMRI, vol. 3, No. 6 Nov./Dec. 1993.

"Gadolinium–enhanced MR Aortography", Prince, Radiology, vol. 191, No. 1, pp. 155–164, Apr. 1994.

"Optimizing Blood Vessel Contrast in Fast Three–Dimensional MRI", Haacke, et al., SMRM Workshop on MR Imaging of Blood Flow, Mar. 13–14, 1989.

"Contrast Enhancement in Abdominal CT: Bolus vs. Infusion", Burgener, et al., AJR, vol. 137, pp. 351–358, 1981.

"MRA Adds Value in Body Imaging",Prince, MR, vol. 5, No. 3, pp. 29–31, Summer 1995.

"3D–MR–Angiographie mit Gd–DTPA", Seiderer, et al., Fortschr. Rontgenstr., 152–153 (1990), pp. 327–332.

"Fast Magnetic Resonance Angiography Using Turbo–FLASH Sequences in Advanced Aortoiliac Disease", Sivananthan, et al., The British Journal of Radiology, vol. 66, No. 792, pp. 1103–1110, Dec. 1993.

"Contrast–Enhanced Magnetic Resonance Tomoangiography: A New Imaging Technique for Studying Thoracic Great Vessels", Revel, et al., Magnetic Resonance Imaging, vol. 11, pp. 1101–1105, Nov. 8, 1993.

"MR Imaging (Including MR Angiography) of Abdominal Aortic Aneurysms: Comparison with Conventional Angiography", Kaufman, et al., AJR, 163, pp. 203–210, Jul. 1994.

"Gadolinium–Enhanced MR Aortography", Prince, Radiology, p. 193, Nov. 1994.

"Gadolinium–Enhanced Magnetic Resonance Angiography of Abdominal Aortic Aneurysms", Prince, et al., Journal of Vascular Surgery, vol. 21, No. 4, pp. 656–669, Apr. 1995.

"Breath–Hold Gadolinium–Enhanced MR Angiography of the Abdominal Aorta and its Major Branches", Prince, et al., Radiology, vol. 197, No. 3, pp. 785–792, Dec. 1995.

"Gadolinium Enhanced MR Imaging of Vascular Stents", Matsumoto et al., Journal of Computer Assisted Tomography, vol. 14, No. 3, pp. 357–361, May/Jun. 1990.

Magnetic Resonance Angiography, Concepts & Applications, Potchen et al., chapter 16, "Magnetopharmaceuticals as contrasts agents", Marchal et al., pp. 305–322, 1993.

"Evaluation of Renal Artery Stenosis with Dynamic Gadolinium–Enhanced MR Angiography: Work in Progress", Rieumont, et al., Radiology, p. 193, Nov. 1994.

"An Extended–Length Coil Design for Peripheral MR Angiography", Rajan et al, Magnetic Resonance Imaging, vol. 9, No. 4, pp. 493–495, 1991.

"Fast MRI with turbo–FLASH Sequences in Aortoiliac Disease", Sivanathan et al., The Lancet, vol. 338, pp. 1090–1091, Oct. 26, 1991.

"The Use of Contrast–Enhanced TurboFLASH Sequences in Aorto–Iliac Disease and Their Comparison with Conventional Angiography", Sivanathan et al., SMRM 1992, Berlin, p. 3108.

"Preliminary Study of Pulmonary Three–Dimensional Time of Flight MR Angiography with Breath–Holding Using a Contrast Medium", Isoda et al., Radiation Medicine, vol. 11, No. 5, Sep.–Oct. 1993, pp. 191–195.

"Fast Three–Dimensional Time–of–Flight MR Angiography with Timed Injection of Contrast Material", Kanal et al., Radiology 1991; vol. 181(P), 119(abstract 169C).

"Fast Three–Dimensional Time–of–Flight MR Angiography with Contrast Bolus Injection", Talagala et al., SMRI 1992, paper ™332.

"Fast RF–spoiled Three–dimensional MR Angiography of Intracranial Vasculature in Scan Times under 1 minute", Talagala et al., Book of Abstracts, SMRM 1991, p. 1021.

"Normal Abdominal Enhancement Patterns with Dynamic Gadolinium–enhanced MR Imaging, Radiology", Mirowitz et al., vol. 180, No. 3, 1991, pp. 637–640.

"Gadolinium Optimized Tracking Technique: A new MRA Technique for Imaging the Peripheral Vascular Tree from the Aorta to the Foot Using One Bolus of Gadolinium", Ho et al., Proceedings of SMRM, Apr. 12–18, 1997, vol. 1, p. 203.

"Fluoroscopically–Triggered Contrast–Enhanced Three Dimensional MR Angiography", Wilman et al., Proceedings of SMRM, Apr. 12–18, 1997, vol. 1, p. 202.

"Moving Bed Infusion Tracking: A New MR Angiographic Technique for Imaging the Peripheral Arteries", Ho et al., Radiology, 1997, vol. 205, Dec. RSNA 1997, p. 301 (abstract 678).

"Bolus Chase Gadolinium–enhanced MRA of the Aorta and Lower Limb Vessels with a 'Stepping Table': Comparison with Catheter Arteriography", Meaney et al., Radiology, 1997, vol. 205, Dec. RSNA 1997, p. 462 (abstract 1356).

"Bolus Chase Gadolinium–enhanced MRA of the Aorta and Lower Extremity Arteries: Technique, Interpretation and Correlation with Arteriography", Meaney et al., Radiology, 1997, vol. 205, Dec. RSNA 1997, p. 559 (Space 0051 VI).

"Bolus Triggered Hepatic Helical CT", Laakso et al., American Journal of Roentgenology, Mar. Supplement 1995, p. 116 (abstract 224).

"Bolus Triggered CT Angiography—First Clinical Results", Kopka et al., American Journal of Roentgenology, Mar. Supplement 1995, p. 132 (abstract 271).

"Smartprep: A Technique for Improving Hepatic Imaging with Helical CT", Silverman et al., Radiology Supplement, Nov. 1994, p. 165 (abstract 260C).

* cited by examiner

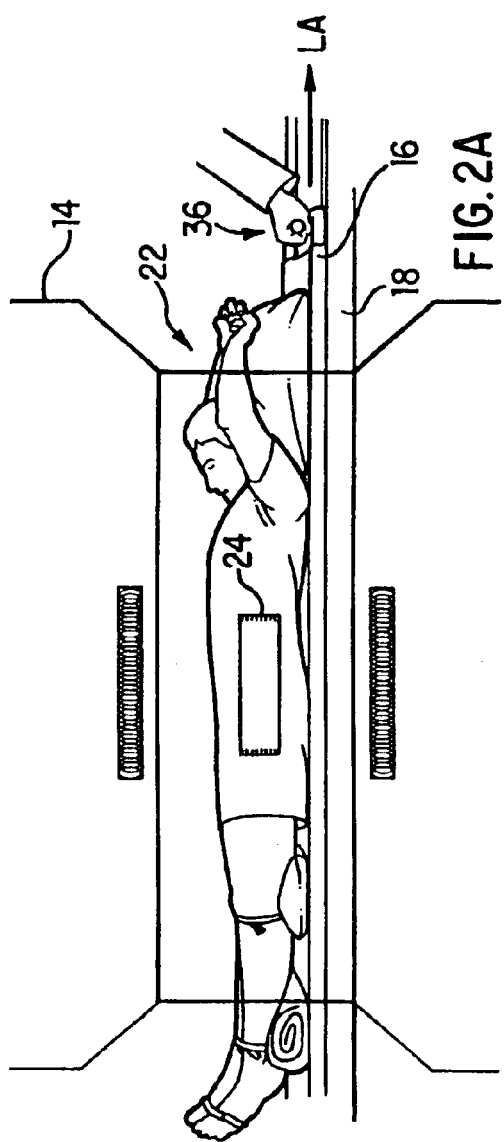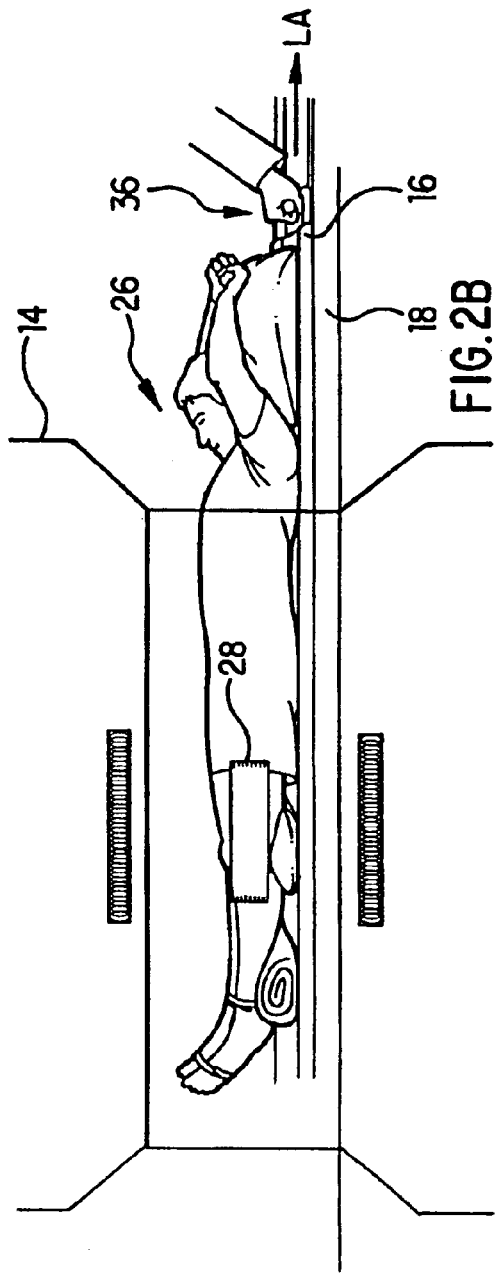

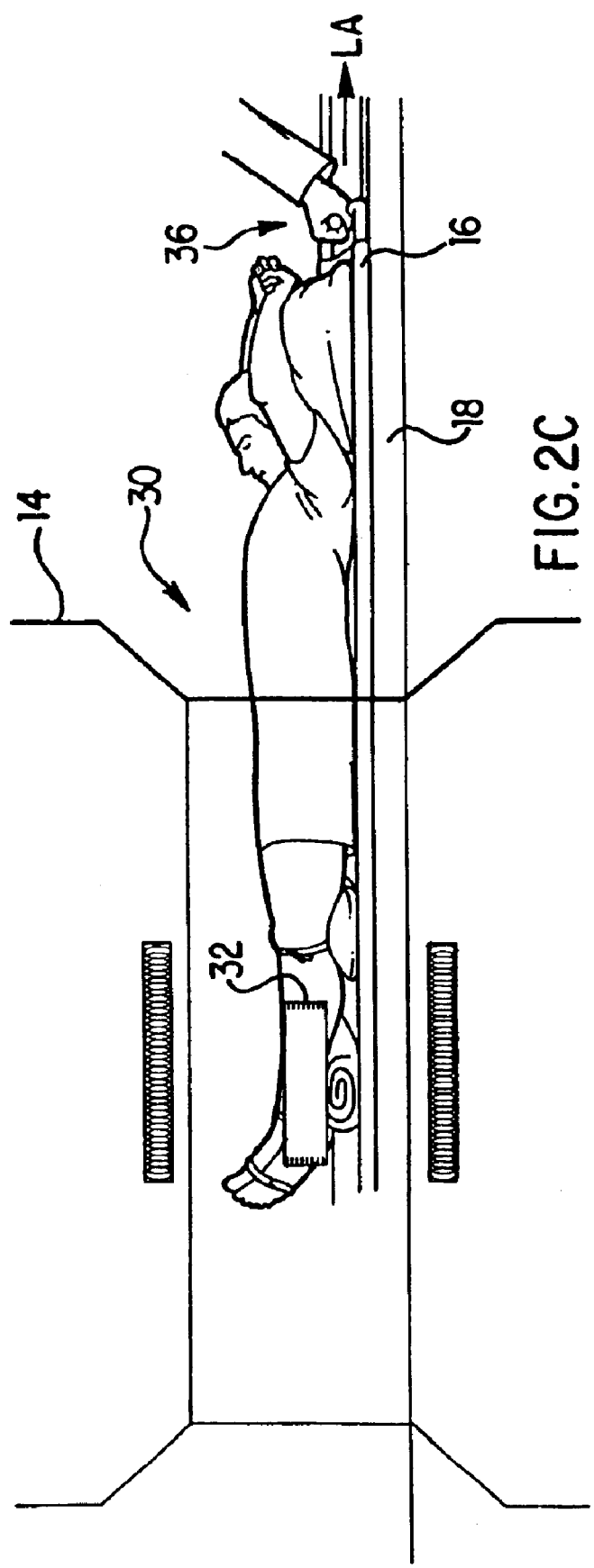

METHOD AND APPARATUS FOR MAGNETIC RESONANCE ARTERIOGRAPHY USING CONTRAST AGENTS

This application is a continuation of application Ser. No. 10/032,860, filed Oct. 23, 2001, (now U.S. Pat. No. 6,564,085), which is a continuation of application Ser. No. 09/309,311 (now U.S. Pat. No. 6,311,085), filed May 11, 1999, which is a continuation of application Ser. No. 08/944,426, filed Oct. 6, 1997, now U.S. Pat. No. 5,924,987.

BACKGROUND OF THE INVENTION

This invention relates to a method of, and apparatus for use in, magnetic resonance imaging; and more particularly, to contrast agent enhanced magnetic resonance arteriography for examining, detecting, diagnosing, and treating arterial diseases and injuries in arteries in the lower extremities, including defining anatomic features relevant to performing arterial surgery for atherosclerotic disease.

Arterial diseases and injuries are common and often have severe consequences including death. Imaging arteries serves to screen, detect and characterize arterial disease before these consequences occur. It also serves to define anatomic features which may provide assistance when performing surgery for atherosclerosis.

Atherosclerosis is a major problem in the aged population, particularly those in developed countries. This disease tends to be progressive in a considerable number of instances and may result in significant morbidity; and, in instances of severe atherosclerotic disease, lower limb amputations and/or mortality.

Early detection of atherosclerosis may lead to a decrease incidence of complications by allowing earlier treatment of arterial stenoses or atherosclerotic disease. Of the conventional techniques, catheter arteriography is the "gold standard" for delineation of the arterial tree of the lower extremities. This technique involves inserting a catheter into the artery of interest (the artery under study) and injecting radiographic contrast, for example, an iodinated contrast, while acquiring radiographs of the artery. Radiographs are commonly referred to as X-rays. The contrast remains in the arteries for a few seconds during which time the arteries appear distinct from both the veins and background tissue in the radiographs.

Although a catheter-based contrast arteriography technique generally provides high quality arterial images, there is a risk of arterial injury or damage by the catheter and its insertion. There may be thrombosis, dissection, embolization, perforation or other injury to the artery itself. Furthermore, such a technique may result in a stroke, loss of a limb, infarction or other injury to the tissue supplied by the artery. In addition, hemorrhage at the catheter insertion or perforation sites may require blood transfusions. Moreover, kidney failure and brain injury may result from the toxic effects of the X-ray contrast.

Because of its invasive nature, cost and complication rate, catheter arteriography is typically not a suitable screening technique for detection of stenoses or atherosclerotic disease. Rather, catheter arteriography is most often used prior to angioplasty or surgical reconstructive procedures—that is, after detection and diagnosis of a stenoses or atherosclerotic disease.

Further, although catheter arteriography is highly accurate under ideal conditions, it often fails to demonstrate distal vessels suitable for bypass in more than half of the patients with severe disease. Additionally, overlapping cortical bone can make interpretation of overlying vessels difficult.

There are several conventional non-invasive tests for diagnosis of peripheral vascular disease including B-mode and color flow Doppler sonography. Sonography provides indirect information of stenoses based on waveforms and velocity measurements. These type of tests require a skilled and experienced examiner to maintain acceptable accuracy and are often problematic in obese individuals. Although imaging from the groin vessels to the level of the mid popliteal artery is possible in many patients, arterial information below the mid popliteal artery is frequently inaccurate. In addition, because sonography provides indirect information of the arterial characteristics, sonography cannot image stenoses directly in the majority of cases. As such, estimation of the degree of luminal stenosis relies on velocity measurements which can often be inaccurate.

Magnetic resonance angiography has several advantages over conventional or catheter arteriography. Magnetic resonance angiography does not use ionizing radiation, and does not require arterial catheterization and sometimes can be performed without contrast agent enhancement. Even when performed using a contrast agent (e.g., gadolinium), magnetic resonance angiography contrast is safer than iodinated contrast arteriography, and it infrequently causes the patient discomfort. In addition, the cost of an magnetic resonance arteriogram is less than a catheter arteriogram. Further, because of its sensitivity to slow flow MRA may be more sensitive in vessels with proximal stenoses.

However, there are several impediments or limitations to use of magnetic resonance angiography as a satisfactory screening tool for imaging of the lower limb vasculature. These impediments or limitations have been documented in, for example, Owen, et al., Magnetic Resonance Imaging of Angiographically Occult Runoff Vessels in Peripheral Arterial Occlusive Disease, N Eng. J Med 1992, 326:157–1581; Owen et al., Symptomatic peripheral vascular disease: Selection of imaging parameters and clinical evaluation with MR angiography, Radiology 1993, 187:627–635; Yucel et al., Atherosclerotic occlusive disease of the lower extremity: prospective evaluation with two-dimensional time-of-flight MR angiography, Radiology 1993,187:635–641; and Borrello, MR Angiography versus conventional X-ray angiography in the lower extremities: Everyone wins, Radiology 1993,187:615–617).

One of the limitations to employing contrast enhanced magnetic resonance angiography for imaging of the lower limb vasculature has been the lack of a suitable coil for imaging of a sufficiently large field-of-view which encompasses the lower extremities. Another potentially more serious problem involves limitations of magnet imaging region. In this regard, the length of the magnet imaging region for conventional magnet resonance apparatus is insufficient to cover the entire anatomical region-of-interest in one acquisition. This can be as much as 120 centimeters in tall patients and even in small patients an imaging field encompassing approximately 90 centimeters is necessary to compete with arteriography which images from above the aortic bifurcation downwards.

Because of the reliance of traditional magnetic resonance arteriography methods on time-of-flight effects, imaging orthogonal to the plane of the vessel necessitates image acquisition in the axial plane. As such, it is necessary to reposition the patient and perform an additional localizer for successive locations down the leg—all of which is time-consuming. In order to maintain spatial resolution, thin slices must be obtained giving poor spatial "coverage" per unit time. Under these circumstances, imaging times may be in excess of one hour and frequently 2 hours for comprehensive imaging of the lower limb vessels. Although acquisition of the 2-D time-of-flight images in the coronal plane would significantly reduce imaging time and therefore cost, imaging in this plane would result in saturation of the flowing blood and non-diagnostic studies.

One solution to the problem of in-plane saturation has been to employ contrast enhanced magnetic resonance arteriography to overcome saturation effects. See, e.g., U.S. Pat. Nos. 5,417,213; 5,553,619; and 5,579,767 (the contents of each are hereby incorporated by reference). Using this technique, acquisition of the central lines of k-space which govern image contrast are acquired during peak arterial enhancement by carefully timing the injection of the contrast agent with the collection of image data which is representative of the center of k-space. A technique of more precisely acquiring the central lines of k-space during peak arterial enhancement by detecting arrival of the gadolinium bolus and initiating data acquisition of data which is representative of the central lines of k-space is described in U.S. Pat. No. 5,590,654. These technique have been shown to be highly accurate compared to arteriography or surgical inspection in the evaluation of abdominal aortic aneurysms, thoracic aorta, renal and mesenteric arteries, and aorta and iliac vessels.

In spite of the high quality images of the abdominal aortic aneurysms, thoracic aorta, renal and mesenteric arteries, and aorta and iliac vessels which have been consistently obtained using contrast enhanced magnetic resonance arteriography, there still remains several problems with using such imaging techniques to evaluate arteries in lower extremities. By using a gadolinium contrast agent, high signal-to-noise images are generated within the body coil. Although this overcomes the problems of both in-plane saturation effects and the necessity for expensive and as yet experimental surface coils, the imaging volume is limited by the largest field-of-view. The field of view, however, is governed by the physical dimensions of the body magnet or coil (typically 48 centimeters or less). Even if this large field-of-view could be used, the increased matrix size necessary to maintain resolution would increase examination time (increased number of phase-encoding steps) and increase echo time (increased frequency-encoding steps), both of which are undesirable. Additionally, the signal-to-noise from the top and bottom ends of the imaging volume would likely be inadequate for diagnostic purposes; and even if adequate images were obtained over the entire imaging volume, the anatomical coverage would still be insufficient for adequate evaluation of the lower extremities.

Although a second sequence centered at a lower level would provide the "missing" diagnostic information, this presents additional concerns of the time dependence of the arterial signal which would likely diminish to a level below that necessary for diagnostic imaging in relation to the time necessary for re-localization and re-prescription of another sequence at another, lower level. This time delay in collecting image data for the second, lower level would be of such a magnitude that enhancement of lower limb veins would complicate interpretation of images and probably render lower extremity arterial imaging non-diagnostic.

As a result, there exists a need for an improved apparatus and method for magnetic resonance arteriography which provides an image of the arteries distinct from the veins and which overcomes the limitations of other techniques. There exists a need for an apparatus and technique which allows preferential imaging of the lower limb arterial tree in a sufficiently short time period to allow imaging without significant venous overlap and without the complications often observed or experienced with catheter arteriography.

In addition, there exists a need for a contrast (e.g., gadolinium) enhanced magnetic resonance arteriography technique which provides essential and accurate anatomic information for arterial reconstructive surgery and which is devoid of contrast-related renal toxicity or catheterization-related complications attending catheter arteriography.

SUMMARY OF THE INVENTION

In one principal aspect, the present invention is a method of imaging arteries in a patient using a magnetic resonance imaging system having an imaging coil and an administered contrast agent. The arteries include a first artery which is located in a first image volume and a second artery in a second image volume.

The method of this aspect of the invention includes positioning the patient in a first location in the imaging coil and then collecting image data of the first image volume including collecting image data which is representative of a center of k-space while a concentration of the administered contrast agent in the first artery is substantially higher than a concentration of the contrast agent in veins and background tissue adjacent to the first artery and while the patient is in the first location. The method further includes re-positioning the patient in a second location in the imaging coil and, then collecting image data of a second image volume, including collecting image data which is representative of a center of k-space while a concentration of the administered contrast agent in the second artery is substantially higher than a concentration of the contrast agent in veins and background tissue adjacent to the second artery and while the patient is in the second location.

The method may further include constructing an image of the first and second arteries using the image data of the first and second image volumes.

In another principal aspect, the present invention is a magnetic resonance imaging system for imaging arteries in a patient using an injected contrast agent of substantially one injection. The arteries include a first artery which is located in a first image volume and a second artery which is located in a second image volume. The system includes an imaging coil and a platform for supporting the patient in a substantially horizontal posture, the platform being moveable with respect to the imaging coil and between a plurality of locations along a longitudinal axis of the platform. The system also includes imaging means for collecting image data of the first image volume while the platform is positioned at a first location and image data of the second image volume while the platform is positioned at a second location.

The image data of the first image volume includes image data which is representative of a center of k-space while a concentration of contrast agent in the first artery is substantially higher than a concentration of contrast agent in veins and background tissue adjacent to the first artery. The image data of the second image volume includes image data which is representative of a center of k-space while a concentration of contrast agent in the second artery is substantially higher than a concentration of contrast agent in veins and background tissue adjacent to the second artery.

In one embodiment, the system further includes means for moving the platform between a plurality of discrete locations along the longitudinal axis.

In another embodiment, the imaging means generates a data collection complete signal in response to completing collection of the image data of the first image volume and wherein the platform, in response to the data collection complete signal, automatically moves from the first location to the second location. In this embodiment, the platform may generate a move complete signal in response to arriving at the second location and wherein the imaging means automatically collects the image data of the second image volume in response to the move complete signal.

In another embodiment, the system includes monitoring means for monitoring a concentration of the injected magnetic resonance contrast agent in a region of interest and wherein the imaging means collects image data of the first image data volume in response to an image acquisition signal. In this embodiment, the system may also include means for generating the image acquisition signal when the magnetic resonance contrast agent in the region of interest is above a predetermined concentration.

In yet another principal aspect, the present invention is a magnetic resonance imaging system for imaging arteries in a patient using an injected contrast agent of substantially one injection. The arteries include a first artery which is located in a first image volume, a second artery which is located in a second image volume, and a third artery which is located in a third image volume. The system includes an imaging coil and a platform for supporting the patient, the platform being moveable along a horizontal axis of the platform between a first location on the longitudinal axis, a second location on the longitudinal axis, and a third location on the longitudinal axis.

The system of this aspect of the invention also includes an imaging unit, electrically coupled to the imaging coil, the imaging unit collects image data of the first image volume while the platform is positioned in the first location and image data of the second image volume while the platform is positioned in the second location, and image data of the third image volume while the platform is positioned in the third location. The image data of the first image volume includes image data which is representative of a center of k-space while a concentration of contrast agent in the first artery is substantially higher than a concentration of contrast agent in veins and background tissue adjacent to the first artery; the image data of the second image volume includes image data which is representative of a center of k-space while a concentration of contrast agent in the second artery is substantially higher than a concentration of contrast agent in veins and background tissue adjacent to the second artery; and the image data of the third image volume includes image data which is representative of a center of k-space while a concentration of contrast agent in the third artery is substantially higher than a concentration of contrast agent in veins and background tissue adjacent to the third artery.

In a preferred embodiment, the system includes a platform moving means for automatically moving the platform between the first, second and third locations. In this embodiment, the imaging unit generates a data collection complete signal in response to completing collection of the image data of the first image volume, and wherein the platform moving means, in response to the data collection complete signal, automatically moves the platform from the first location to the second location.

In another embodiment, the imaging unit generates a data collection complete signal in response to completing collection of the image data of the second image volume, and wherein the platform moving means, in response to the data collection complete signal, automatically moves the platform from the second location to the third location, wherein the platform moving means generates a move complete signal in response to arriving at the third location and wherein the imaging unit automatically collects the image data of the third image volume in response to the move complete signal.

In another embodiment, the imaging unit constructs an image of the first, second and third arteries using the image data of the first, second and third image volumes.

In yet another embodiment, the first image volume overlaps the second image volume by less than about 25% and the second image volume overlaps the third image volume by less than about 25%.

BRIEF DESCRIPTION OF THE DRAWINGS

In the course of the detailed description of preferred embodiments to follow, reference will be made to the attached drawings, in which:

FIGS. 2A–C are cross-sectional views of the platform, the patient, and the imaging coil apparatus for three locations of the platform of a given imaging sequence;

DETAILED DESCRIPTION

The present invention is a technique of, and system for, imaging vascular anatomy over distance considerably greater than the maximum practical field of view of a magnetic resonance imaging system. The technique and system of the present invention acquires image data of a plurality of image volumes which are representative of different portions of the patient's body. The image data of each image volume includes image data which is representative of the center of k-space. The center of k-space may be characterized as 10% to 75% of the total k-space data which, as indicated above, corresponds to the lowest spatial frequency information. Thus, the image data which is representative of the center of k-space of a plurality of image volumes is collected while the concentration of the contrast agent in the artery contained within the image volume is substantially greater than the concentration of contrast agent in veins and background tissue adjacent to the artery.

The present invention provides preferential enhancement of arteries relative to adjacent veins and background tissue by correlating the collection of a predetermined portion of data of a magnetic resonance contrast image with the arterial phase of the magnetic resonance contrast enhancement over a series of acquisitions, each acquisition being representative of a different portion of the arterial system (e.g., abdominal aorta, femoral, popliteal, and tibial arteries). The arterial phase of the contrast enhancement may be described as a period of a maximum, substantially higher and/or substantially elevated contrast concentration in the artery (arteries) relative to adjacent veins and background tissue. The arterial phase of contrast enhancement may also be described as a period during which the concentration of contrast agent in the artery of the region of interest is about a factor of two greater than a base line or pre-injection response from the region of interest (i.e., the response of the region of interest to a series of magnetic resonance pulses prior to administration of a magnetic resonance contrast agent to the patient).

The system and technique of the present invention collects image data in a series of acquisitions to examine, detect, diagnose, and treat arterial diseases and injuries of arteries, including arteries in the lower extremities (e.g., the femoral arteries). The present invention correlates the collection of image data which is representative of the center of k-space for plurality of image volumes with the arterial phase of contrast enhancement in the arteries within the image volumes. The images constructed from the image data of the image volumes may be combined in a way in which they provide a "mosaic" of a significant portion of the patient's arterial system (e.g., the abdominal aorta, and femoral, popliteal, and tibial arteries).

Figure 1:
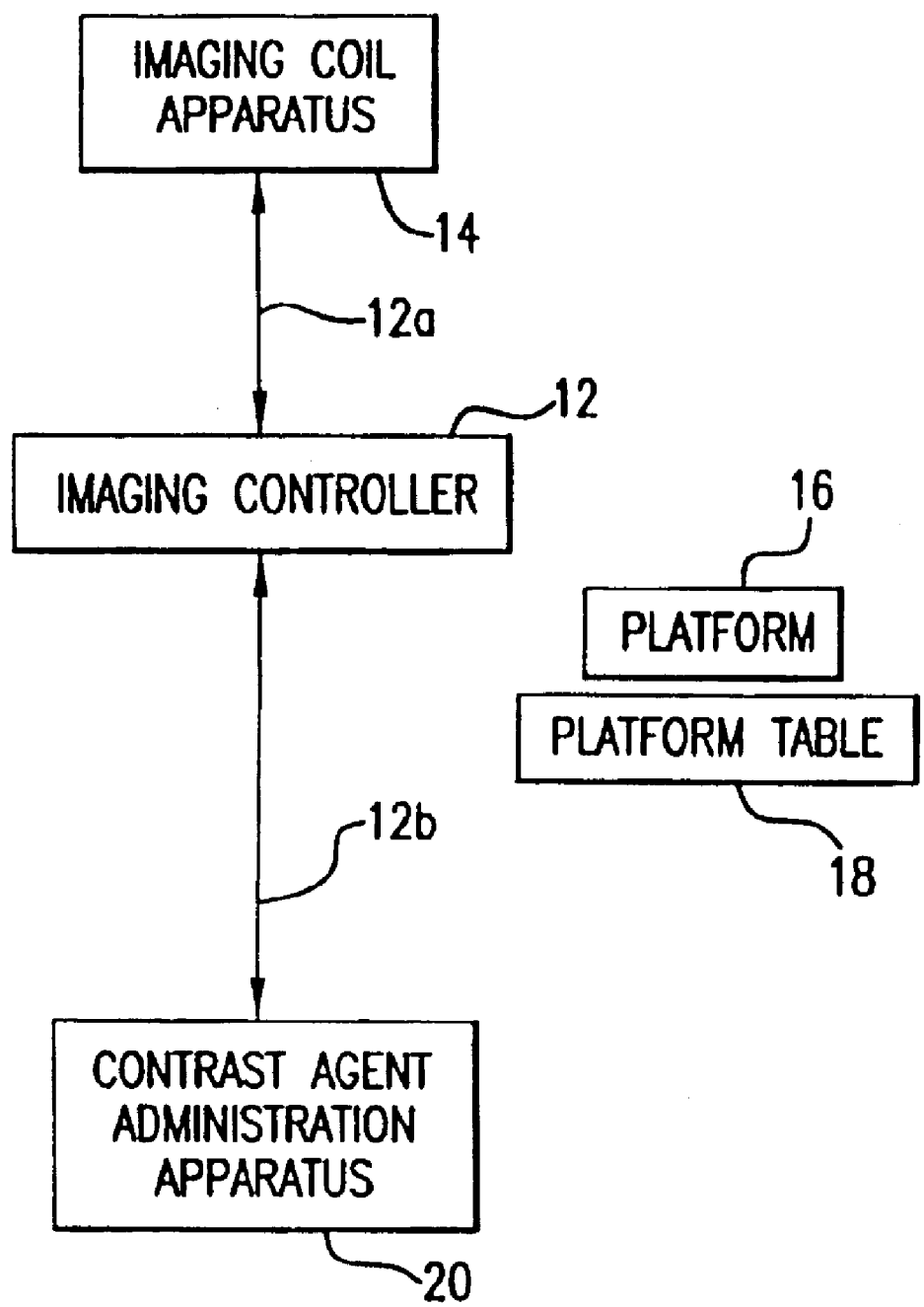
FIG. 1 is a block diagram representation of an embodiment of the magnetic resonance imaging system according to the present invention.

With reference to FIG. 1, a magnetic resonance imaging system 10 of one embodiment of the present invention includes an imaging controller 12 and an imaging coil apparatus 14 for collecting image data which is used to generate an image of the region of interest. The imaging controller 12 and imaging coil apparatus, 14 may be a commercial magnetic resonance imaging system (including hardware and software), for example General Electric's Horizon system, Siemens' Vision system, or Phillips' Gyroscan system. These imaging systems are suitable for imaging an animal body, for example, a human. In addition, the software used with the commercial magnetic resonance imaging system may be modified to accommodate several embodiments described herein, including collecting image data which is representative of the center of k-space in the beginning, middle or end of the imaging sequence. Moreover, when the image data which is representative of the center of k-space is collected (e.g., beginning, middle or end of the imaging sequence) may be altered from image sequence to image sequence.

With reference to FIGS. 1 and 2A, the magnetic resonance imaging system 10 further includes a platform 16 for supporting a patient. The platform 16 is positioned on a platform table 18. The platform 16 is moveable along the platform table 18 and may be positioned in a plurality of locations along the table 18. The platform table 18 includes a portion which is located within the imaging coil apparatus 14 to permit the platform 16 to be positioned at locations along a longitudinal axis LA of the platform 16 within the imaging coil apparatus 14.

In operation, the patient is placed on the platform 16 and secured thereto in order to prevent or limit movement of the patient relative to the platform 16. The platform 16 is then placed at a first location 22 in the imaging coil apparatus 14 such that a field of view of the system 10 encompasses a first artery (e.g., the abdominal aorta).

A magnetic resonance contrast agent (e.g., gadolinium) is then administered to the patient using a contrast agent administration apparatus 20 (FIG. 1) which will be discussed below. While the platform 16 is located in a first location 22, the imaging controller 12 collects image data which is representative of a first image volume 24. The first image volume 24 is defined by the first location 22, the field of view of the image coil apparatus 14, and the number of slices acquired by the controller 12. Here, image data of the first image volume 24 includes image data which is representative of the center of k-space collected while the concentration of contrast agent in the first artery is substantially greater than the concentration of contrast agent in veins and background tissues adjacent to the first artery. Thus, image data representative of the center of k-space of the first image volume 24 is collected during the arterial phase of contrast enhancement. Under these circumstances, the first artery is preferentially enhanced relative to veins and background tissues adjacent to the first artery.

With reference to FIG. 2B, after collecting at least the image data which is representative of the center of k-space of the first image volume, the platform 16 is moved along the platform table 18 to a second location 26 such that a field of view of the system 10 encompasses a second artery (e.g., the femoral and/or popliteal artery). While the platform 16 is located in a second location 26, the imaging system 10 collects image data of the second image volume 28. The image data of the second image volume 28 includes image data which is representative of the center of k-space collected while the concentration of contrast agent in the second artery is substantially greater than the concentration of contrast agent in veins and background tissues adjacent to the second artery. The second artery, like the first artery, is preferentially enhanced relative to veins and background tissues adjacent to the second artery.

With reference to FIG. 2C, after collecting at least the image data which is representative of the center of k-space of the second image volume, the platform 16 is again moved along the platform table 18 to a third location 30 such that a field of view of the system 10 encompasses a third artery (e.g., the tibial artery). While the platform 16 is located in a third location 30, the imaging controller 12 collects image data of the third image volume 32. The image data of the third image volume 32 is image data which is representative of the center of k-space collected while the concentration of contrast agent in the third artery is substantially greater than the concentration of contrast agent in veins and background tissues adjacent to the third artery. Like the first and second arteries, the third artery is preferentially enhanced relative to veins and background tissues adjacent to the third artery.

This process may be repeated for as many imaging sequences as is necessary to collect image data of the image volumes which are necessary for imaging a desired portion of the arterial system or until the arterial phase of contrast enhancement resulting from the injected contrast agent expires.

Figure 2D:
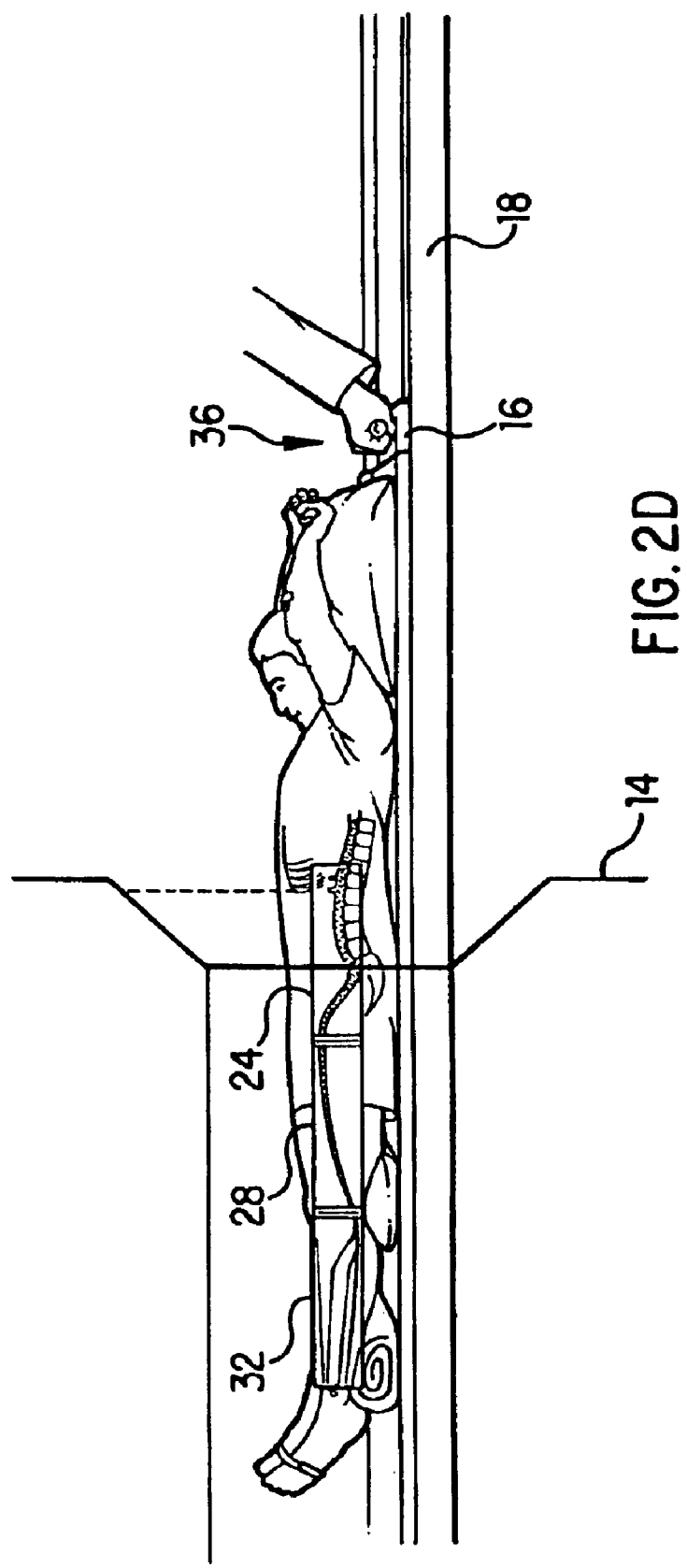
FIG. 2D is an illustration of the relationship between the three image volumes corresponding to the three locations of the imaging sequence of FIGS. 2A–C.
Figure 8A:
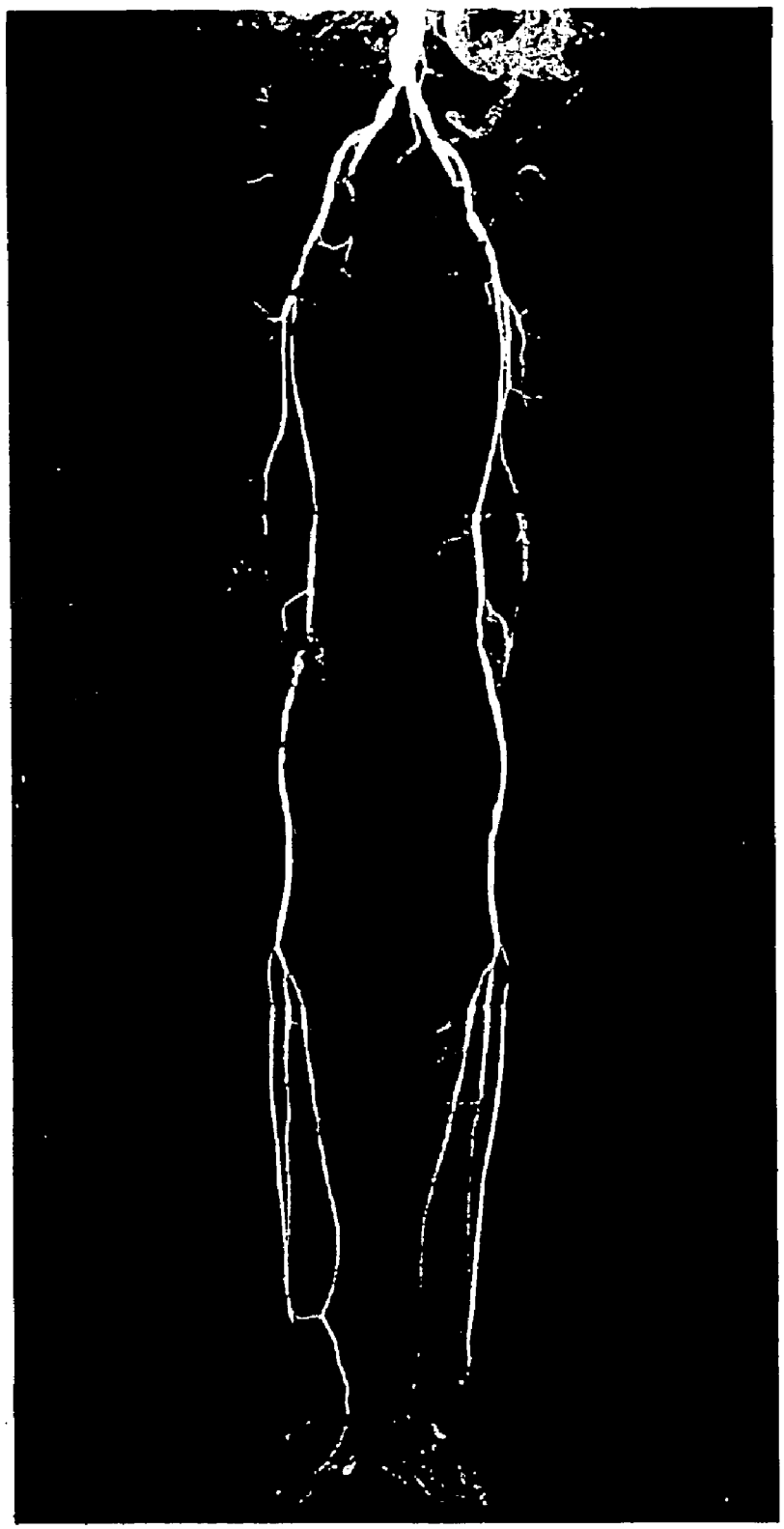
FIGS. 8A and 8B is an illustrative example of a magnetic resonance arteriography image of a patient using the technique and system of the present invention. The image depicts the arterial tree in the lower abdomen, the thighs, and the calves and a portion of the feet. This image was constructed using three image volumes in a manner described and illustrated herein for FIGS. 2A–2D.
Figure 8B:
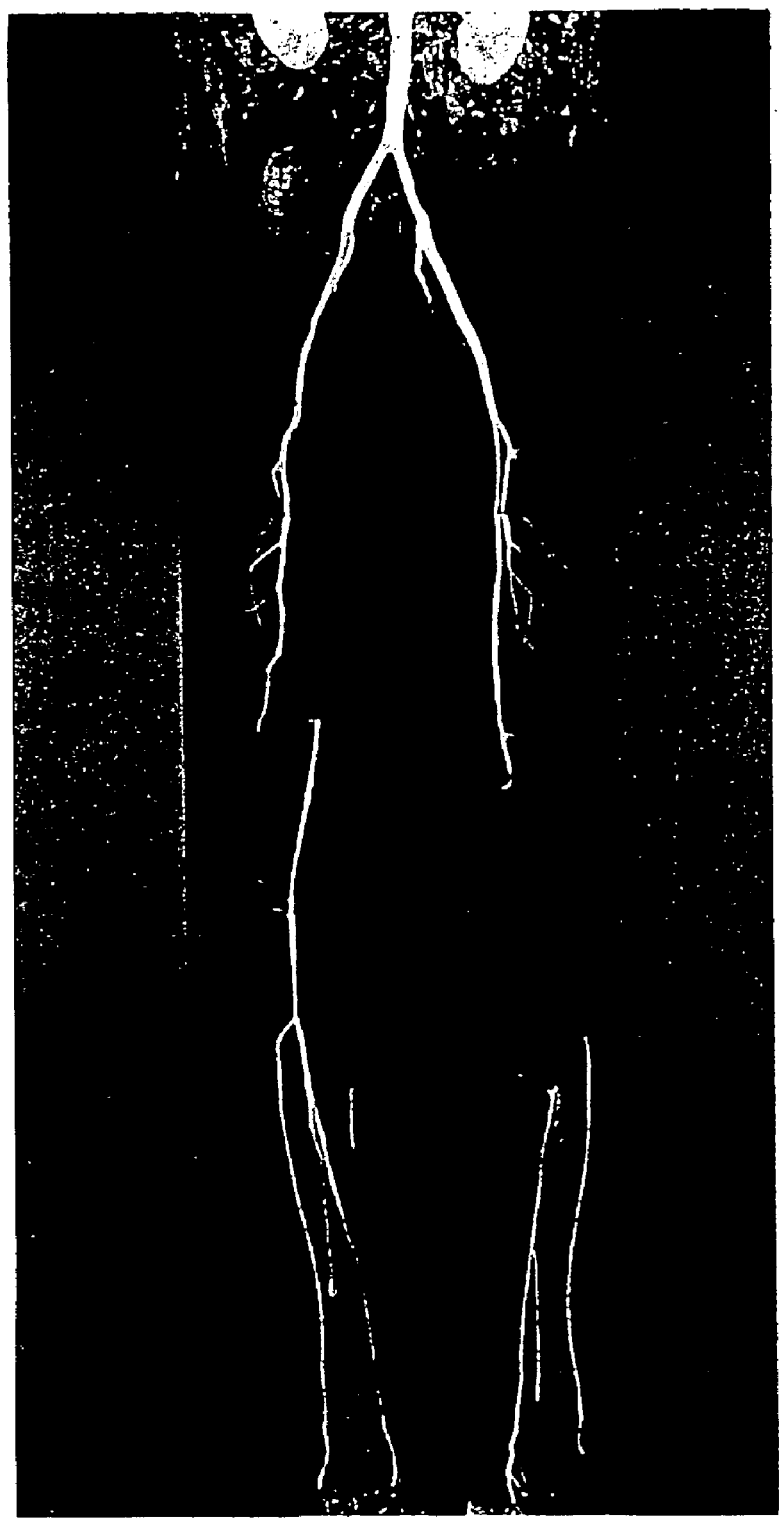

With reference to FIGS. 2D, 8A, and 8B, the images constructed using the image data collected during the imaging sequences at the first, second and third locations may then be combined in a mosaic-like fashion to provide a composite image of the arterial system captured within the first, second and third image volumes. Using the composite image of the first, second and third image volumes, a physician may examine, detect, and treat arterial diseases and injuries of arteries which may be observed in the images, including those arteries in the lower extremities (e.g., the abdominal aorta, femoral, popliteal, and tibial arteries).

The image volumes may be aligned so that the edge of a given image volume coincide with the edge of a preceding, adjacent image volume. In this way, the image volumes are aligned with little to no overlap.

In one preferred embodiment, however, the image volumes are aligned to provide overlap between a given image volume and the preceding, adjacent image volume. For example, as mentioned above, after collecting image data of the first image volume 24 at the first location 22, the platform 16 is moved to the second location 26. The second location 26 is selected so that within the second image volume 28 there is a portion of the first image volume 24. Further, after collecting image data of the second image volume 28 at the second location 26, the platform 16 is moved to the third location 30. The third location 30 is selected so that within the third image volume 32 there is a portion of the second image volume 28.

Overlapping adjacent image volumes may compensate for limitations of several commercially available imaging systems, where the edge or periphery of the field of view may not provide a homogeneous magnetic field (i.e., there may be some distortion of that field). Further, such overlap provides a higher degree of confidence that no portion of an artery is inadvertently excluded from the composite image constructed from the images acquired at the plurality of locations.

The amount of overlap may depend, for example, upon the size of the field of view, the size of the patient, the characteristics of the imaging coil apparatus 14 (e.g., the homogeneity of the field) and the degree of confidence desired by the physician. In a preferred embodiment, where the field of view is approximately 48 centimeters, the imaging system 10 is a GE Horizon system, and where imaging at a more caudal level, typically centered over the mid-thighs of the patient, the overlap may be in the range of 2 to 8 centimeters.

Stated more generally, however, in a preferred embodiment, a given image volume is arranged/defined in order to provide less than 25% overlap with the preceding, adjacent image volume. In a more preferred embodiment, the amount of overlap between a given image volume and the preceding image volume is between 5% to 15%.

In a preferred embodiment, the present invention employs one contrast agent injection or a series of injections in rapid succession (i.e., each injection followed immediately by another injection)—both of which are hereby defined as substantially one injection. The contrast agent may be injected rapidly, in a bolus type manner, may be injected over a portion of image data acquisition of one image volume, may be injected over a portion of image data acquisition including a plurality of image volumes, or may be injected over a substantial portion of image data acquisition of all of the image volumes. The rate of injection and/or how the contrast is injected, however, is selected to facilitate the collection of image data which is representative of the center of k-space for each image volume during the arterial phase of contrast enhancement. That is, these injection parameters are chosen to provide preferential enhancement of arteries relative to adjacent veins and background tissue for acquisition of the image data of each image volume, each image volume mapping a different portion of the arterial system (e.g., abdominal aorta, femoral, popliteal, and tibial arteries).

Figure 3:
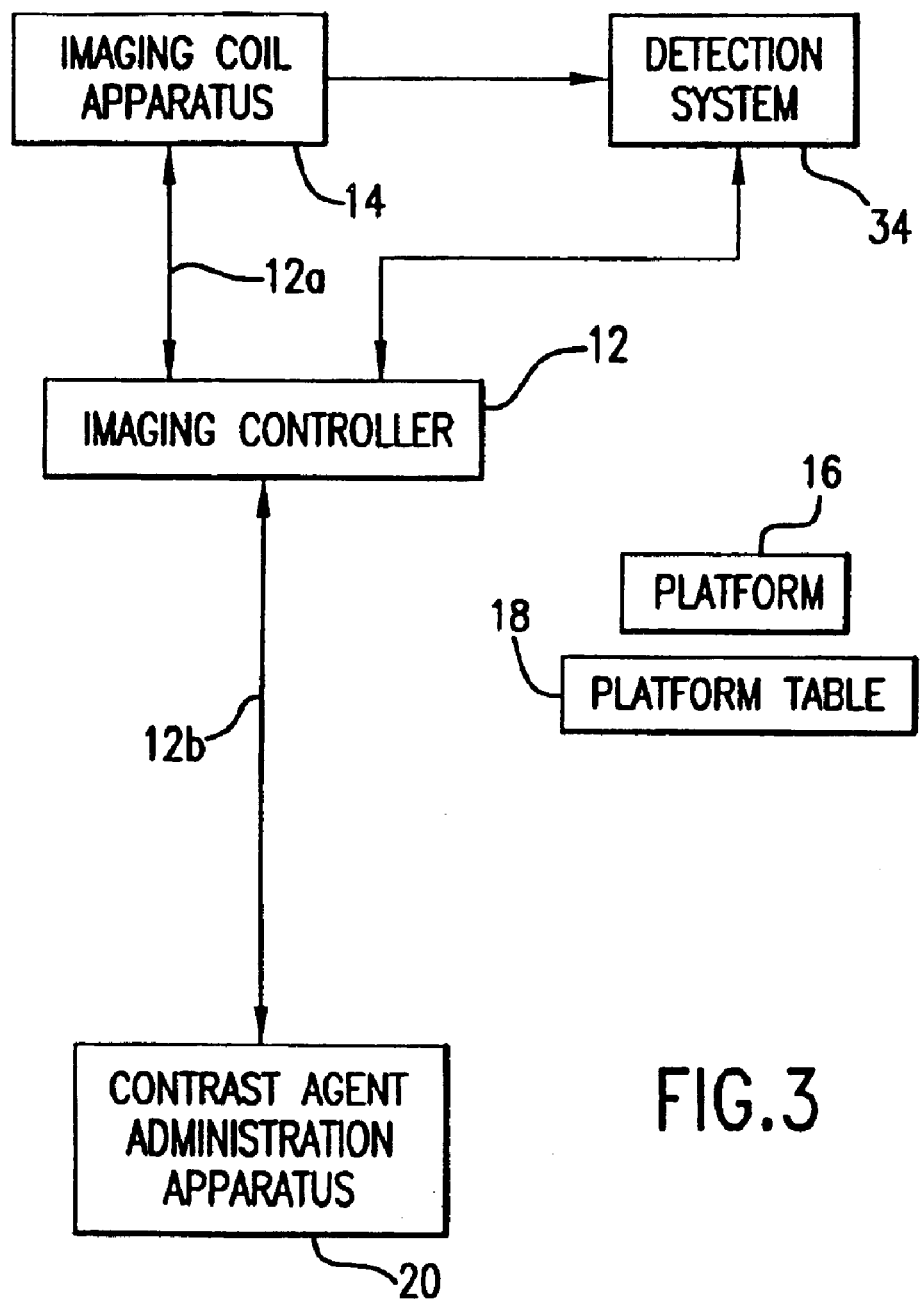
FIG. 3 is a block diagram representation of another embodiment of the magnetic resonance imaging system according to the present invention.

With reference to FIG. 3, in another embodiment of the present invention, the magnetic resonance imaging system 10 may further include a detection system 34 for synchronizing the collection of a predetermined portion of image data (e.g., the center of k-space) with the arterial phase of contrast enhancement. In this embodiment, the detection system 34 monitors and detects the relative concentration of magnetic resonance contrast agent in the region of interest (artery and tissues in a region of interest). By doing so, the imaging controller 12 may more precisely synchronize the collection image data which is representative of the center of k-space with the arterial phase of contrast enhancement for one, some or all of the image volumes.

As discussed in detail in U.S. Pat. No. 5,590,654, which is hereby incorporated by reference, the detection system 34 facilitates precise synchronization between the collection of a predetermined portion of image data and a portion of the arterial phase of contrast enhancement. The detection system 34 compares the response of a region of interest before the administration of magnetic resonance contrast agent (e.g., gadolinium) to the patient to the response of the region of interest during and/or after administration of the contrast agent. When a characteristic change in the response to the magnetic resonance pulse is measured by the detection system 34, the imaging system 10 collects a predetermined portion of image data (e.g., data representative of the center of k-space).

In particular, in one embodiment, the patient is secured to the platform 16 and the platform 16 is positioned in a first location 22. Prior to the administration of a magnetic resonance contrast agent, the imaging system 10 applies a series of magnetic resonance pulses (radio frequency pulses) to a first region of interest in the patient. The detection system 34 measures or determines a base line or pre-contrast response of the region of interest (artery and/or tissues in the region of interest) to that series of pulses. The series of magnetic resonance pulses are applied to the patient to tip the longitudinal magnetization of protons in the region of interest and measure the response of the region of interest before administration of the contrast agent to the patient. The response signal from the region of interest is monitored using a variety of coils of the imaging coil apparatus 14 and is measured by the detection system 34.

After the base line or pre-contrast response is measured, the contrast agent may be administered to the patient. Thereafter, the detection system 34 measures (continuously, periodically or intermittently) the response from the region of interest to detect the "arrival" of the contrast agent in the region of interest. In this regard, the magnetic resonance imaging system 10 applies a series of magnetic resonance pulses and the detection system 34 evaluates the response from the region of interest. When contrast agent "arrives" in the region of interest (artery or arteries of interest), the detection system 34 detects a characteristic change in the response from the region of interest to the magnetic resonance pulses; that is, the detection system identifies a characteristic change in the radio frequency signal emitted from the region of interest. This characteristic change in radio frequency signal from the region of interest indicates that the contrast agent has "arrived" in the artery/arteries in that region.

In one embodiment, upon detecting the arrival of the contrast agent in the first region of interest, the detection system 34 instructs the imaging controller 12 to initiate collection of image data of the first image volume, including image data which is representative of the center of k-space. After collecting image data which is sufficient to construct the first artery within the first region of interest, the platform 16 is moved to the second location such that a field of view of the system 10 encompasses a second artery.

While the platform 16 is located in a second location, the detection system 34 may be employed to determine when the contrast agent "arrives" in the second region of interest. Upon detecting the arrival of contrast in the second region of interest, the detection system 34 may instruct the imaging controller 12 to collect image data which is representative of the center of k-space. This provides more precise synchronization of the collection of such image data with a concentration of contrast agent in the second artery which is substantially greater than the concentration of contrast agent in veins and background tissues adjacent to the second artery. Under these circumstances, the second artery is preferentially enhanced relative to veins and background tissues adjacent to the second artery.

It should be noted that the detection system 34 need not be used to determine when the contrast agent "arrives" in all of the regions of interest for each location the of platform. Thus, in another embodiment, the detection system 34 may be employed only to synchronize collection of image data of the first image volume but not for the second image volume 28. Rather, when the platform 16 is positioned in the second location 26, the imaging controller 12 may automatically collect image data which is representative of the center of k-space for the second image volume 28.

In those instances where the injection of the contrast agent is of a bolus type (i.e., rapid injection), the characteristic change in the response to the magnetic resonance pulses may indicate that the region of interest is in or is "entering" the arterial phase of the magnetic resonance contrast enhancement. Where the contrast agent is injected over a substantial portion of the imaging sequence, detecting the arrival of the contrast agent may indicate that the region of interest is entering the arterial phase of contrast enhancement or will be entering the arterial phase some time in the future depending on a "time delay" as described below.

In a preferred embodiment, the detection system 34, upon sensing the region of interest is entering the arterial phase of contrast enhancement (e.g., contrast concentration in the region of interest is above a predetermined level), may instruct the imaging controller 12 of the magnetic resonance imaging system 10 to initiate acquisition of data which is representative of the center of k-space. The concentration of the contrast in the region of interest may be detected in a number of different ways including, for example, a change in the shape of the responsive radio frequency signal, a change in the shape of the signal envelope and/or a change in its amplitude.

In another embodiment, an operator may observe a change in the shape of the radio frequency signal envelop and/or a change in its amplitude measured by the detection system. In response, the operator may instruct the imaging system 10 to initiate an imaging sequence including collecting image data which is representative of the center of k-space by the magnetic resonance imaging system 10. In this embodiment, the operator monitors the detection system to observe the characteristic change in the response from the region of interest to the plurality of pulses from the imaging system; and, upon observing such a change, the operator may engage the imaging system to begin collecting image data which is representative of the center of k-space (i.e., the low spatial frequency magnetic resonance image data), or a portion thereof, of the predetermined imaging sequence.

Under the circumstances where the detection system 34 (or operator) instructs the imaging system 10 to collect image data which is representative of the center of k-space upon detecting the start of the arterial phase of contrast enhancement, the magnetic resonance imaging pulse sequence may be arranged such that the central portion of k-space data is collected in the beginning or near the beginning of the sequence and the periphery of k-space is collected either before or after collection of k-space. This may enhance synchronization between the arterial phase of contrast enhancement and the collection of image data which is representative of the center of k-space. Moreover, arranging the sequence such that the central portion of k-space data is collected in the beginning or near the beginning of the sequence insures that a sufficient amount of data which is representative of the center of k-space is collected during the arterial phase of contrast enhancement.

It should be noted that General Electric Medical Systems markets and sells a commercially available detection software package under the tradename FasTrack. The FasTrack product is designed to operate on General Electric's Horizon magnetic resonance imaging system. The FasTrack software package triggers acquisition of the central portion of k-space data when the arterial concentration in a region of interest is elevated. With little to, no modification, the FasTrack detection system may be employed, in conjunction with a magnetic resonance imaging system, to perform the detecting functions of present invention.

In those instances where the arterial phase is "long", there may be time to collect the entire image data set (the center of k-space and the periphery thereof) during the arterial phase.

However, in those instances where the arterial phase is brief relative to the overall imaging sequence (i.e., collection of image data for all of the imaging volumes), there may not be time to collect the entire image data set (the center of k-space and the periphery thereof) during the arterial phase. Under this circumstance, collection of image data which is representative of the center of k-space is synchronized with the period of a maximum and/or substantially elevated concentration in the artery(ies) of interest relative to adjacent veins and background tissues for each image volume of the overall imaging sequence. The periphery of k-space (or that portion of k-space which was not collected dynamically) may be collected before or after dynamically collecting the center of k-space at the plurality of locations.

For example, the patient may be placed in the first location, second location and third location before administration of contrast agent and the periphery of k-space (or that portion of k-space which was not collected dynamically) may be collected at the corresponding locations. Then, with the patient positioned in the first location, the operator may administer the contrast agent to the patient. The imaging system 10 then collects the center of k-space of the first image volume which is generally defined by the first location.

After collecting the center of k-space of the first image volume, the platform 16 is moved to the second location such that a field of view of the system 10 encompasses a second artery. While the platform 16 is located in a second location, the imaging system 10 collects image data which is representative of the center of k-space of the second—image volume. And so on.

In a preferred embodiment, the type or form of injection of the contrast agent is intravenous. The injection of the contrast is performed intravenously in order to eliminate or reduce the complications associated with the catheterization required for arterial injections.

The specific site of injection is important for several reasons. The site of injection should be remote from the "region of interest"; that is, the region that is to be scanned. For example, when imaging the abdominal aorta and arteries in the lower limbs, intravenous injection of the contrast agent into an arm vein is preferred. Use of a leg vein should be avoided. Further, there may be some benefit in avoiding the antecubital fossa because the patient may bend the elbow during a long (3–5 minute) period of injection which may result in extravasation of the contrast into the subcutaneous tissues. As a result, under this condition, a forearm or upper arm vein may be preferable.

It should be noted, however, that when the injection is by rapid infusion (i.e., less than one minute in duration) the antecubital vein may be preferred because of its close proximity to the heart compared to the forearm and hand.

In those instances where an artery in the arm is to be imaged, the site of the injection may be a leg vein or a vein in the opposite arm. Here, the site of injection is remote from the "region of interest", i.e., the artery in the arm.

Figure 4:
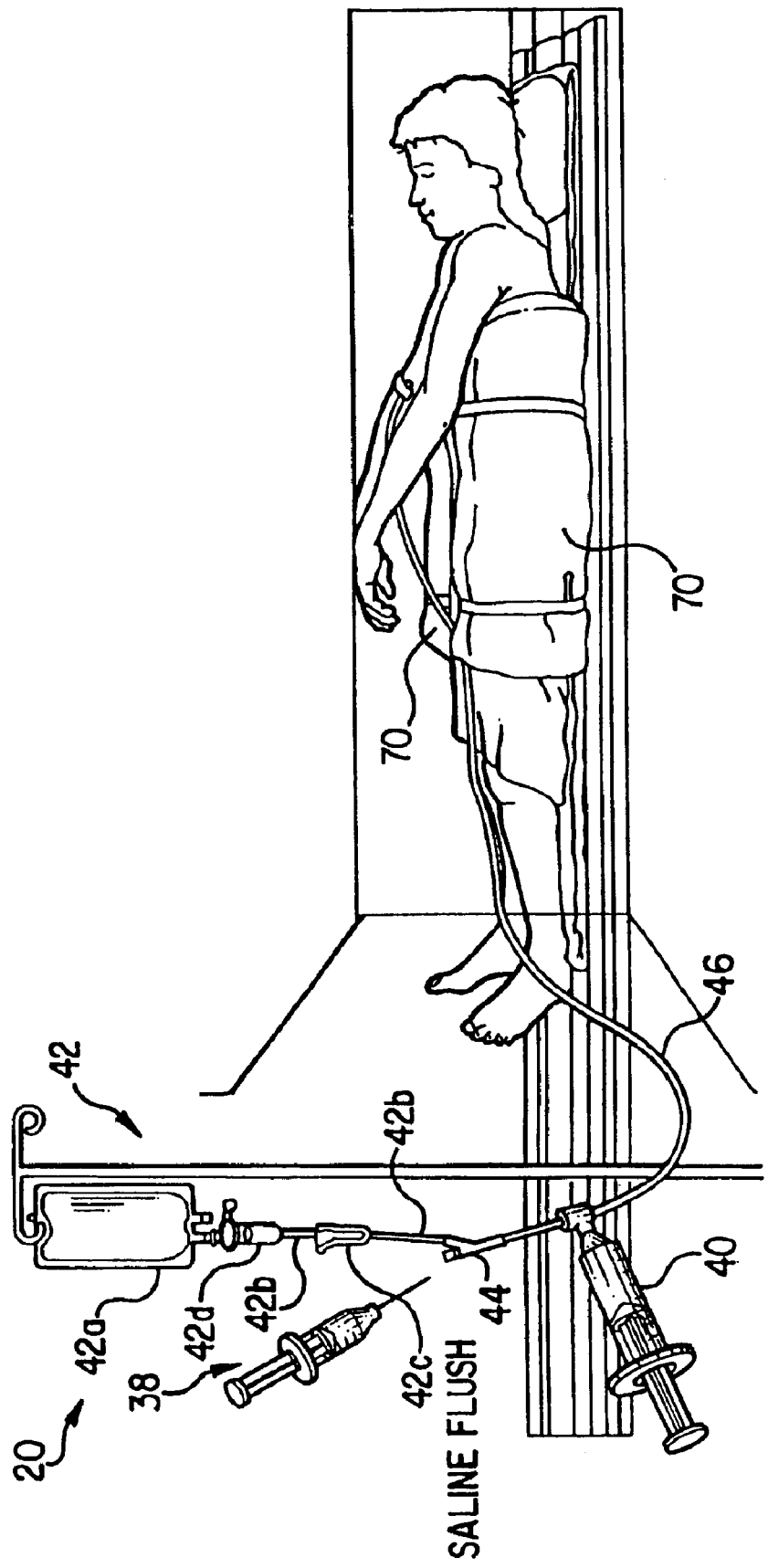
FIG. 4 is an illustration of a preferred embodiment of a contrast agent administration apparatus.

A preferred embodiment of a contrast agent administration apparatus 20 is illustrated in FIG. 4. In this embodiment, a syringe 38 is loaded with a magnetic resonance contrast agent. A 3-way stopcock 44 permits rapid contrast agent (e.g., gadolinium) injection without risk of retrograde flow. Another side port of the stopcock 44, further from the patient, accommodates an additional syringe 40 which may be employed as a rapid saline flush immediately following the contrast injection.

A drip chamber 42d allows the operator to observe that the tubing 46 is intravascular and working properly. In this regard, a bag of normal saline 42a, or other suitable fluid, is connected to the proximal end of the tubing 46 via a drip chamber 42d. The operator may observe the drip chamber 42d to determine whether the intravenous line is working properly. A roller clamp 42c may be employed to prevent too rapid saline flow into the patient.

It should be noted that a bag of saline 42a which is too large may be harmful to the patient should the entire volume of saline be administered to the patient; using a small bag of saline, accidental administration of the entire bag will not be harmful. Typically, a 250 cc bag of fluid is suitable for providing enough fluid to last for the entire exam and to avoid injury to the patient if there is accidental release of the entire quantity of the fluid into the circulation in a short span of time (e.g., in less than 15 minutes).

The dynamic infusion of contrast may be facilitated by using tubing 46 which reaches inside the magnet and which allows the operator infusing contrast to stand comfortably outside the magnet environment where it is possible to watch a clock and/or have access to control panels for the imaging system 16 to initiate the scan. With a sufficient length of tubing, the operator may comfortably use both hands to perform the infusion; generally one hand holds the syringe plunger and the other hand holds the syringe chamber.

In those embodiments where the operator is positioned outside the magnet environment, at least 2 to 6 feet of tubing may be required to reach outside the magnet environment. A side port for gadolinium infusion should be located about 2 to 6 feet away from the end of the tubing which is at the intravenous puncture site. A second side port a few inches further away is also useful to allow sufficient space for both gadolinium filled and saline filled syringes to be attached simultaneously. This allows the gadolinium infusion to be immediately followed with the saline flush without any delay for switching syringes. By placing one-way valves in the tubing upstream from each side port, the fluids (contrast agent and flush) are forced to flow in the correct direction without risk of retrograde flow in the tubing. One of the one-way valves should be between the two side ports so that the contrast agent may not "backup" into the other syringe used for flush. This is particularly important when the gadolinium is injected so rapidly that a high infusion pressure is required. The most proximal one-way valve could be replaced with a clamp or other mechanism to impede flow.

It may also be useful to have an extra port (a third port) positioned close to the distal end of the tubing where it attaches to the patient. This port can be used for treating any reaction that the patient might have to the contrast being infused. By having this third port close to the patient, it minimizes the distance that medicines must travel in order to reach the patient's circulation. It is anticipated that in the event of a contrast reaction, the patient would be immediately removed from the magnet so that this third port would be readily accessible.

Proximal and distal ends of the tubing should have standard medical type luer locking connectors. The distal end should have a male connector. It is useful if this distal end has a locking mechanism to prevent the tubing from becoming detached from the intravenous catheter during the increased pressure of fast infusions. A flow meter that provides feedback to the operator about the contrast infusion rate may be useful.

The inner diameter of the tubing 46 may be important. The tubing's inner diameter may be selected to strike a balance between a sufficient diameter to minimize flow resistance but not so large a diameter that there is a large dead space. Dead space is the volume of tubing between the IV site in the patient's arm and the point where the syringe 38 attaches to the tubing 46.

In one embodiment, a tubing inner diameter of about 0.08 inch strikes a good balance between the need to minimize resistance and the need to minimize dead space for tubing that is about 6 feet long with gadopentetate dimeglumine or gadodiamide as contrast agents. The tubing 46 may be made of plastic, rubber or any other suitable (non-magnetic) material. The tubing 46 should be pliable so that it can easily adjust or conform to the path of the intravenous site on the patient's arm to outside the magnet environment. In some situations it is also useful if the tubing assumes a natural coil configuration so that it will tend to stay wound up. This helps to avoid having the intravenous tubing becoming intertwined with other tubing or wires in the general vicinity of the magnet and imaging system 16.

Figure 5A:
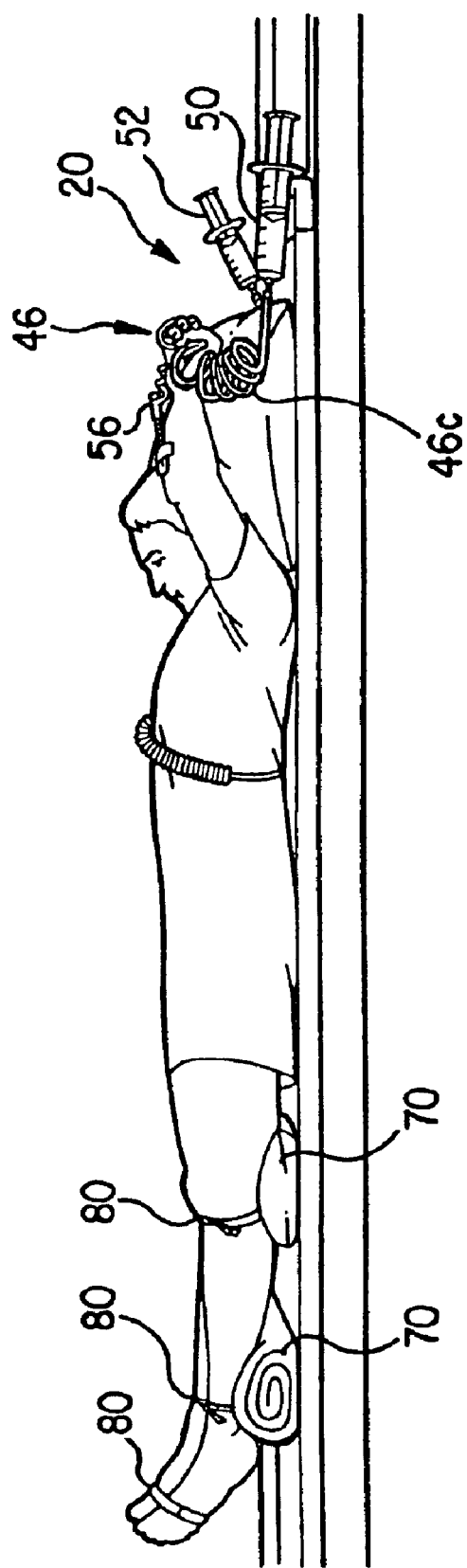
FIGS. 5A and 5B are illustrations of a preferred embodiment of a contrast agent administration apparatus according to the present invention.
Figure 5B:
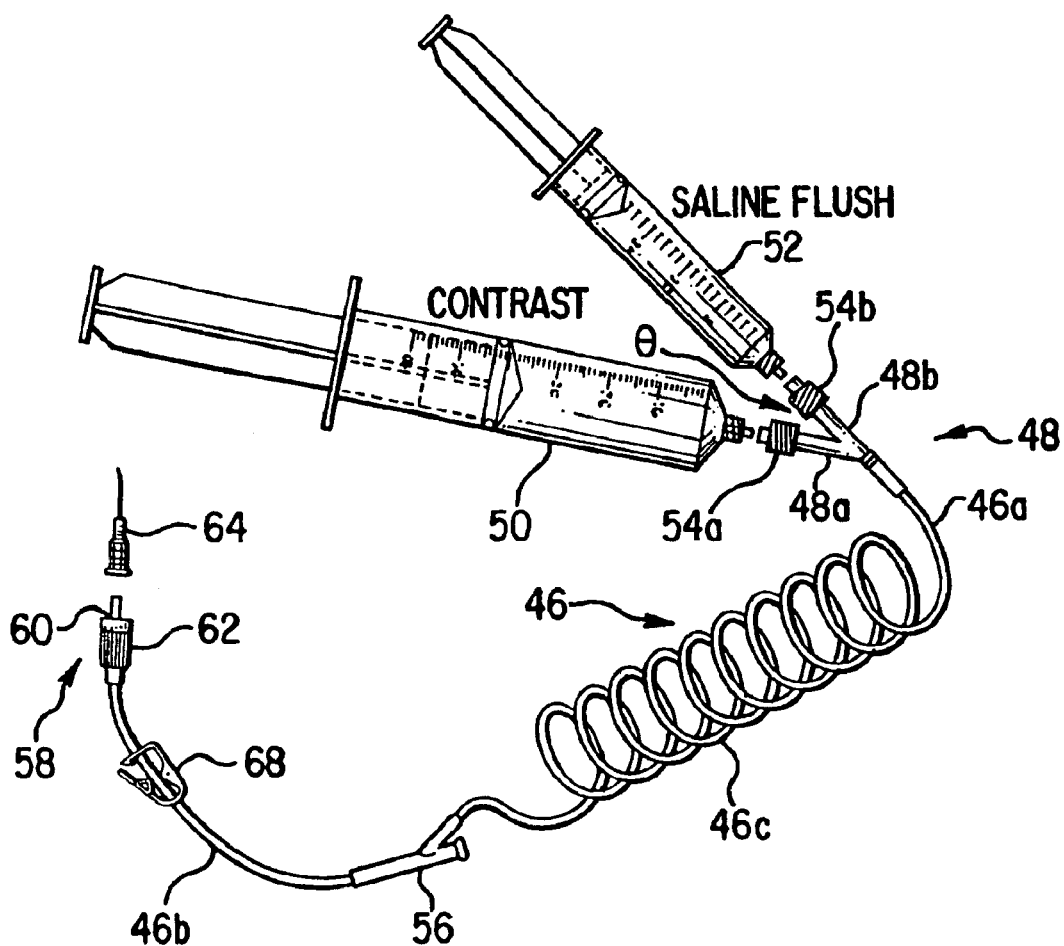
Figure 6:
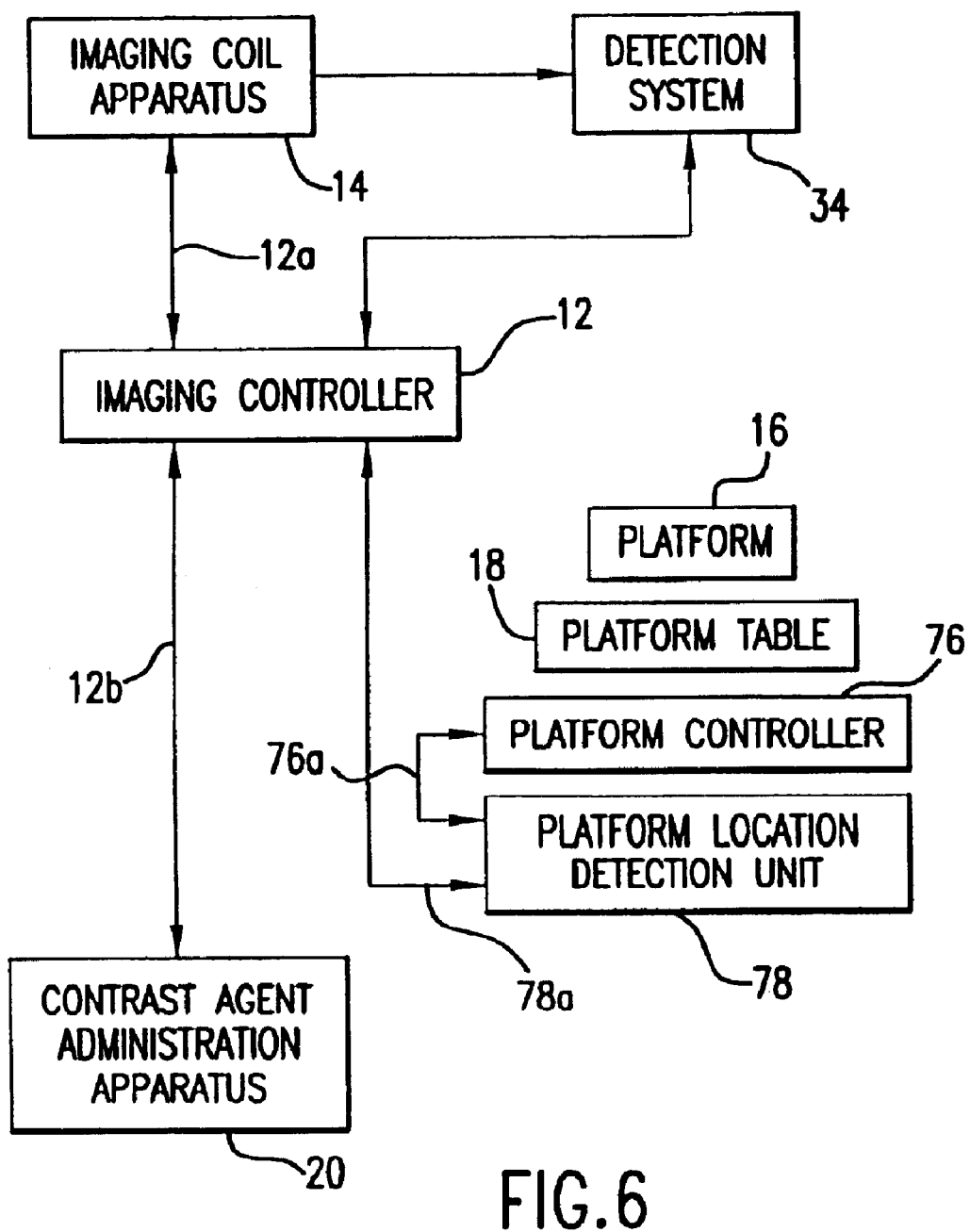
FIG. 6 is a block diagram representation of another embodiment of the magnetic resonance imaging system according to the present invention.

Another embodiment of the contrast agent administration apparatus 20 is illustrated in FIGS. 5A and 5B. With reference to FIGS. 5A and 5B, the contrast agent administration apparatus 20 includes tubing or conduit 46. In this embodiment, the tubing 46 includes a first end 46a, a second end, 46b, and a substantially coiled portion 46c.

The substantially coiled portion 46c of tubing 46 is in a "tightly wound" or "coiled" state when no external forces are applied to the tubing 46. Coiled portion 46c provides a number of advantages to tubing 46 including allowing the operator to readily adjust the tubing 46 to different lengths while in the magnetic resonance suite. In this regard, the operator may inject the contrast agent and fluid flush from different locations in the suite (i.e., at different distances from the patient's IV and the magnet) as well as readily adjust the tubing to different distances that the tubing must reach inside the magnet based on a particular patient with reduced risk that tubing 46 will become intertwined with other tubing or wires in the general vicinity of the patient, magnet and/or imaging system 16 and/or damaged by exposure to traffic in the suite.

The extent to which the tubing 46 is coiled may be adjusted to suit the operator's needs as well as suit the conditions of the magnetic resonance suite. In a preferred embodiment, the tubing 46 is between 0.5 and 3 meters in length (when fully extended). In a more preferred embodiment, the tubing 46 is about 2 meters in length (when fully extended). In these embodiments, tubing 46 is made of a plastic (e.g., Polyvinylchloride ("PVC")) or other nonmagnetic material and is substantially transparent so that the operator may observe fluid injection air bubbles or flow.

As mentioned above with reference to the contrast agent administration apparatus 20 of the embodiment of FIG. 5B, the inner diameter of tubing 46 is an important parameter and should be selected according to a number of factors including flow resistance and dead space. In this regard, the inner diameter of tubing 46 should be selected to be sufficiently large to provide minimum resistance to fluid flow and sufficiently small to provide minimum dead space.

Here the inner diameter of the tubing 46 should be selected to avoid excessive resistance to fluid flow during injection. In particular, the inner diameter of the tubing should be large enough to avoid an increase to flow resistance which may impact, for example, the rate of injection and the ease of injection (i.e., the effort expended by the operator while injecting the fluids).

Further, the inner diameter of tubing 46 should be selected to minimize unnecessary dead space. Here, the inner diameter of the tubing should be selected to be small enough to minimize the dead space of tubing 46. The dead space in tubing 46 has a direct impact upon the amount of contrast needed for a particular MRA procedure.

The dead space in the tubing set may also impact the timing of the arterial phase which is critical to data acquisition of the present invention. In this regard, the greater the dead space the greater the time differential between initiation of contrast agent injection by the operator and subsequent introduction of the contrast agent into the patient.

In a preferred embodiment, when injecting gadolinium, gadopentetate dimeglumine, gadoleridol or gadodiamide, the inner diameter of tubing 46 should be between about 0.04 inches and 0.12 inches. In a more preferred embodiment, the inner diameter of tubing 46 is between about 0.06 inches and 0.10 inches. In an even more preferred embodiment, the inner diameter of the tubing is about 0.08 inches; as mentioned above with respect to the apparatus illustrated in FIG. 5B, such a diameter seems to strike a balance between the need to be large enough to minimize flow resistance and yet still small so as to minimize dead space (i.e., a balance between a need to minimize resistance and the need to minimize dead space for tubing that is about 2 feet long with gadolinium, gadopentetate dimeglumine, gadoleridol or gadodiamide as contrast agents).

Tubing 46 should also have a sufficient thickness and hardness to prevent expansion or rupture during injection (i.e., when under pressure of injection) and to prevent kinking during operation. In one embodiment, the tubing wall thickness is greater than about 0.01 inches. In a preferred embodiment, the tubing wall thickness should be between about 0.02 inches and 0.08 inches. In a more preferred embodiment, the tubing wall thickness of tubing 46 is about 0.04 inches and the hardness is about 80 on the Shore A Hardness scale (ASTM D-2240).

The contrast agent administration apparatus of FIG. 5B further includes a multiport adapter 48 located at the first end 46a of the tubing 46. In a preferred embodiment, the multiport adapter 48 includes two input ports 48a and 48b which are adapted to receive standard type syringes 50 and 52, respectively. The two ports 48a and 48b are configured near one another to allow an operator to quickly switch from injecting a contrast agent (e.g., gadolinium) to injecting a fluid flush (e.g., saline) after all of the contrast agent has been introduced into the tubing (i.e., the syringe filled with contrast is empty).

In operation, the configuration of the multiport adapter 48 of FIG. 5B, allows the operator to rapidly inject the contrast agent (i.e., gadolinium) and immediately follow the contrast agent injection with a fluid flush (i.e., saline) with little delay so as to maintain a tight, continuous bolus of the contrast agent.

In a preferred embodiment, the multiport adapter 48 is a two port "Y" bifurcate fabricated from PVC. The ports 48a and 48b are female type input ports which accept standard type syringes. The input ports 48a and 48b are arranged to extend from the base of the multiport adapter 48 at an angle of greater than 10 degrees and less than 45 degrees. In a more preferred embodiment, the longitudinal axis of the first input port 48a and the longitudinal axis of the second input port 48b form an angle ($\theta$) of greater than about 30 degrees and less than about 40 degrees. Under these circumstances, the input ports are configured to allow each input port to accommodate a syringe at the same time (one syringe containing a contrast agent and another containing a fluid flush)

In another preferred embodiment, the input ports 48a and 48b include one-way, check valves 54a and 54b. The one-way, check valves 54a and 54b prevent fluid flow from one input port through the base of the multiport adapter 48 and out the other port (i.e., retrograde flow in the adapter 48). Thus, in operation, valves 54a and 54b preclude the contrast agent (e.g., gadolinium) injected in the contrast port 48a from backing out the flush port 48b and vice-versa.

The dead space within the input ports should be minimized in order to increase the robustness of the tubing apparatus as well as decrease the amount of contrast necessary for a procedure. In a preferred embodiment, the input ports have a dead space which is less than about 1 milliliter.

With continued reference to FIG. 5B, the administration apparatus further includes a medicinal fluid input port 56. Input port 56 is located near the patient end of the tubing 46 (i.e., near second end 46b of the tubing 46) and is designed to permit the operator/physician to rapidly inject medication to the patient in the event of a medical emergency (e.g., a reaction to the contrast agent). Locating medicinal fluid input port 56 close to the patient provides the advantage of minimizing the distance that medicines must travel in order to reach the patient's circulatory system.

The administration apparatus of FIG. 5B further includes a locking mechanism 58. The locking mechanism 58 permits the tubing apparatus to be securely attach to the patient's IV, which may be, for example, an angiocatheter. In a preferred embodiment, the locking mechanism 58 is a male luer locking mechanism having a male luer protector 60 and a male luer swivel 62. In this embodiment, the male luer locking mechanism 58 is attached to the patient's angiocatheter 64 and prevents the tubing apparatus from detaching from the angiocatheter under pressure from the contrast agent and fluid flush infusions.

The administration apparatus may also include a pinch clamp 68 to provide further control of fluid injection. In this regard, the pinch clamp 68 may be used to stop fluid flow immediately for example at the completion of the procedure or during a failure. For example, should the locking mechanism 58 fail for whatever reason, the pinch clamp 68 may be used to prevent or restrict further fluid flow. Similarly, the pinch clamp 68 may be used to restrict fluid flow after the locking mechanism 58 is decoupled or unlocked from the catheter, for example, at the completion of a procedure.

In one embodiment, the pinch clamp 64 may also be used to further synchronize or match the arterial phase of contrast enhancement with the collection of image data which is representative of the center of k-space. That is, the operator may initially fill the tubing with contrast up to approximately the location of the pinch clamp. The clamp 68 is then closed to prevent premature release of the contrast. Then when the optimum moment arrives for injecting contrast, the pinch clamp 68 is release and the injection is completed. Under this circumstance, the time delay in delivering the contrast agent to the patient (and the onset of the arterial phase of contrast enhancement) due to the tubing apparatus is reduced; this reduction may facilitate better synchronization of the arterial phase of contrast enhancement with the collection of image data being representative of the center of k-space.

Further, the contrast agent administration apparatus of FIG. 5B may also include a flow rate indicator to provide the operator an indication of a rate of administration (injection rate) of the contrast agent to the patient. Here, the operator may visually or audibly observe the rate of flow of the contrast agent to more accurately control the rate of injection of the contrast agent into the patient.

The flow rate indicator may be a drip chamber, Pitot probe, or implemented using an optical type sensor (e.g., a Dopler ultrasound probe). The flow rate indicator may also be a electromechanical type sensor which may surround the tubing 46, and/or may be a rotating device in contact with the syringe. Such mechanisms permit an accurate measurement with little to no impact on the injection of the fluid.

Further, the administration apparatus 20 of FIG. 5B may also include a bubble remover which substantially eliminates air bubbles in the fluids in tubing 46 from being introduced to the patient. In this regard, the bubble remover may be located between the medicinal input port 56 and the patient to substantially eliminate bubbles which travel from the syringe and/or tubing 46 to the patient. The bubble remover may be a membrane-like structure which filters out bubbles in the fluid traversing tubing 46.

In some magnetic resonance suites, an opening exists in the wall dividing the magnet of the imaging apparatus and the control equipment (i.e., computer and other electronic devices). In these situations, standard infusion pumps (containing metal, magnetized material and electronic circuits) can be used from outside of the MR suite to implement the methods described herein.

In one preferred embodiment, a pump manufactured by Abbott, the Life Care 5000, may be implemented. The Life Care 5000 draws drugs (e.g., contrast agent) directly from a bottle and preloads it into a long length of tubing. The operating parameters of the Life Care 5000 may be preprogrammed to execute numerous infusion rates.

In another preferred embodiment, the injection rate for contrast is matched with the mapping of k-space so that a maximum or substantially elevated arterial gadolinium concentration correlates with acquisition of image data corresponding to the center of k-space. That is, the operating parameters of the pump may be pre-programmed to provide an injection rate for contrast agent which is matched with the mapping of k-space so that a maximum or substantially elevated rate of infusion occurs about 10–40 seconds prior to the collection of image data corresponding to the center of k-space.

The operating parameters of the pump may also be controlled by the detection system 34 and/or the imaging controller 12. The timing of a maximum, elevated or substantially elevated rate of injection may be controlled by the detection system 110 in order to more accurately synchronize the collection of image data which is representative of the center of k-space to a maximum, elevated or substantially elevated concentration of contrast in the artery of interest. This embodiment is discussed in more detail below.

This type of configuration offers several advantages including: (1) the contrast agent (gadolinium) need not be removed from its shipping containers into an intermediate container, for example, a syringe; (2) the programmability of the pump allows variable injection rates providing for a maximum rate at the peak when the center of k-space is being mapped (which may be the most critical period during image acquisition); (3) operator control of the operating parameters. Moreover, the Life Care 5000 may be coupled to the detection system 34 to facilitate the mapping of k-space by the imaging system 16 with the arterial phase of contrast enhancement in the region of interest.

It should be noted that the Life Care 5000 Pump may not be ideally suited for implementing all of the techniques described herein. For example, such deficiencies include the rates of injection of the pump, the degree of programmability of the flow delivery characteristics of the pump, and allowing the pump to administer contrast from multiple containers which will permit multiple 20 cc vials to be used.

It should be noted that other contrast agent administration apparatus may be suitable for implementing the techniques of the present invention. For example, the apparatus illustrated and described in FIGS. 5A and 5B of U.S. Pat. No. 5,590,654 may also be used in the present invention.

When implementing longer pulse sequences (greater than 2 minutes) or pulse sequences which collect image data representative of the center of k-space some time after initiation of image data collection, it is important that no contrast be administered prior to magnetic resonance scan since the contrast may leak into the background tissues and cause degradation of the image. If some paramagnetic contrast or other magnetic resonance contrast has been administered prior to imaging, it may be useful to delay the arterial scan until this contrast has been excreted by the patient, in order to increase the probability of obtaining optimal images.

An exception to this requirement is when a small test dose of contrast or the like (sodium dehydrocholate, saccharin or indocyanine green) is used to determine the circulation time prior to performing the dynamic injection with imaging. By infusing a small test dose of a few milliliters and then imaging rapidly the region of interest, it is possible to determine the time interval between contrast infusion and contrast arrival in the artery. This time may then be used to guide timing for the image acquisition in that it may facilitate more accurate correlation between the injection of the contrast agent and the acquisition of the data representative of the center of k-space when the imaging system 10 collects such data in the middle of the scanning sequence. Thus, this time should roughly equal the time between the middle of the infusion and the moment of acquisition of the center of k-space for short infusions.

In those instances where the imaging system 10 employs pulse sequences having very short data acquisition periods, the contrast agent may be injected before the initiation of collecting image data. Short pulse sequences may be characterized as those sequences for which the time required for contrast to circulate from injection site to the artery of interest becomes a significant fraction of the imaging time, for example, data acquisition periods of less than 2 minutes. Under this circumstance, injection of the contrast agent before acquisition of image data is necessary to allow circulation of the contrast agent in the patient and thereby correlate a maximum or substantially elevated arterial concentration with the collection of image data representing the center of k-space. As discussed above, the relative timing between the administration of the contrast agent and the collection of image data representing the center of k-space should be adapted to account for the injection mechanism employed, the location of the artery of interest, the size of the artery of interest, and the physical condition of the patient. For example, the contrast may be administered about 10–40 seconds before collection of image data to account for venous blood in the arm to circulate through the heart and lungs to reach the artery of interest. Thus, the amount of time before acquisition of image data may depend on the configuration of the contrast delivery mechanism, the relative location of the artery of interest, the relative size of the artery of interest, and the condition of the patient, including the age of the patient. Employing these considerations in selecting and controlling the timing of the injection provide a more accurate alignment between the acquisition of data representative of the center of k-space and a period of maximum or substantially elevated contrast concentration in the artery of interest relative to adjacent veins.

When employing the conventional imaging sequence which maps k-space in the middle of the scan, in a preferred embodiment, a constant infusion should begin within a few seconds of initiation of the scan process. The contrast infusion should end about 20 or more seconds before the completion of the scan; this allows the intravenously injected contrast to circulate through the heart and into the arteries. A chaser of normal saline or other fluid may be used to insure injection of the entire dose of the paramagnetic contrast (e.g., gadolinium) and, in addition, to insure that there is sufficient venous return to propel the injected contrast to the heart. In a preferred embodiment, the contrast infusion rate is matched with the mapping of k-space so that the maximum arterial gadolinium concentration occurs during acquisition of the center of k-space. This may permit injecting over a shorter period of time to achieve either a higher injection rate or a lower contrast dose.

In one preferred embodiment, the magnetic resonance contrast agent is injected by the administration apparatus 20 in a bolus manner and the imaging sequence, implemented by the imaging system 10, collects data which is representative of the center of k-space at or near the beginning of the sequence. Under this circumstance, in order to correlate, on a repeatable basis, a maximum or substantially elevated arterial concentration of the contrast agent in the artery of interest with the collection of image data corresponding to the center of k-space, the detection system 34 monitors or measures the response from the region of interest to detect the arrival of the contrast agent in that region. Upon detecting the arrival of the contrast agent in the region of interest, the imaging system 10 may initiate (immediately or shortly thereafter) collection of image data representative of the center of k-space. The center of k-space corresponds to the low spatial frequency data which dominates image contrast.

In a preferred embodiment, the period of a maximum or substantially elevated rate of infusion of the magnetic resonance contrast agent to the patient is adapted according to the size of the artery of interest in order to correlate with the period of the collection of image data corresponding to the center of k-space to the period of the arterial phase of contrast enhancement. In this regard, where the artery of interest is relatively large (e.g., the aorta), a period of a substantially elevated or maximum injection rate may overlap for a smaller fraction of the total image time than where the artery is relatively small (e.g., renal). For example, when imaging larger arteries, the administration of the contrast agent may include a period of a substantially elevated or maximum rate of contrast which provides a substantially elevated or maximum arterial concentration for less than 50% of the period during which the system collects image data corresponding to the center of k-space; and preferably at least 20%.

Where the artery of interest is relatively small, it is preferable that a period of maximum or substantially elevated rate of injection provide a maximum or substantially elevated concentration of the contrast in the artery of interest for more than 50% of the period of mapping the center of k-space.

In another preferred embodiment, the magnetic resonance contrast agent is injected rapidly in a bolus manner and the imaging sequence implemented by the imaging system 10 collects image data which is representative of the center of k-space at or near the beginning of the sequence. Upon detecting the arrival of the contrast agent in the region of interest (by the operator or detection system 34), the imaging system 10 may initiate the imaging sequence and collection of image data representative of the center of k-space.

In a preferred embodiment, the legs and arms of the patient are positioned in such a manner that the arteries to be imaged (e.g., the abdominal aorta, femoral artery, and tibial artery, as well as the intervening arteries) are within a relatively small image volume during scanning. With reference to FIG. 5A, where the vasculature from the supra-renal aorta to the level of the foot arteries is to be imaged, the imaging volume must be of sufficient thickness to account for variations in vertical positioning of the arteries to be imaged. The course or path of the arteries do not follow a straight line in the sagittal plane from aorta to foot. Rather, height of those arteries vary considerably. As such, the imaging volume should be sufficiently thick to include all of the arteries at the maximum to minimum anticipated heights. By raising certain limbs (e.g., the legs and the feet), the arteries in those limbs will have less of a vertical deviation from arteries in the torso.

In a preferred embodiment, appendage cushion 70 is positioned under the legs and knees as well as the ankles and feet in order to raise the legs and feet and reduce the size the image volume which is necessary to encompass the arteries in those limbs. Here, the arteries in the abdomen, thighs, calves, ankles and feet are somewhat level. Under these circumstances, a 2 to 4 inch thick image volume may be sufficient to properly and fully image the arteries in the aforementioned regions of the body.

The appendage cushions 70 also provide an additional advantage in that they provide the patient with a stable support for the thighs, knees, calves, ankles and feet so that there is little to no movement of the lower limbs during imaging. This will lead to a significant reduction in artifacts caused by patient movement.

In a preferred embodiment, the appendage cushions 70 are comprised of a non-magnetic material, low density material. The appendage cushions 70 may be shaped in a conformal nature to that of the patient's body that is to be engaged (e.g., posterior portion of the knee). This shape provides for a more stable configuration so that there is little to no movement of the appendage cushions 70 and/or the patient relative to the platform 16. Further, the appendage cushions 70 may be secured to the patient and/or the platform prior to imaging using a non-magnetic strapping mechanism, for example, a velcro strap or similar material/mechanism.

It should be noted that the appendage cushions 70 may also be formed using a blanket or pillow. Under these circumstances, the blanket or pillow easily conforms to the portion of the patient's body which is engaged by the blanket or pillow.

To further reduce lower limb movement, in a preferred embodiment, the feet, ankles and calves are bound together using non-magnetic strapping 80, for example, a velcro strap. Restraining the relative movement of the lower limbs may provide a more stable posture for the patient so that there is little to no movement of the limbs during imaging. As mentioned above, this will lead to a significant reduction in artifacts which result from patient movement.

As for the arms, with reference to FIG. 4, by placing appendage cushions 70 along either side of the patient's torso, the arms are elevated or lifted up in the air. This has several important effects. First, by lifting the arms, the intravenous site of contrast agent injection is elevated thereby creating a "down hill" path for the contrast agent which assists venous return. Under this circumstance, the contrast agent more rapidly enters the central veins to achieve a faster and more predictable circulation time. The circulation time is the time required for contrast agent (e.g., gadolinium) to circulate from the site of infusion through the body to the artery(ies) of interest.

An additional advantage of employing the appendage cushions 70 is that such an arrangement prevents the arms or other stuff from getting into the region along side the patient where it could result in aliasing (wrap-around artifact) caused by the imaging the torso with a coronally oriented volume.

In one embodiment, the cushions 70 may be made of foam or other material that has a low density of hydrogen nuclei. This is to ensure that the cushions 70 do not create much signal or noise during imaging. The length of the cushions 70 should be long enough to keep the arms up along the entire length of the torso. It may be useful in patients with wide hips and narrow torsos to make the cushion thinner in the region of the hips. Alternatively, the cushions may be short enough so that it comes down to the hips but does not overlap the hips.

In a preferred embodiment, the appendage cushions 70 are 8 cm thick of non-magnetic material, low density material. The appendage cushions 70 may be rectangular in shape and may be secured to the patient and/or the platform prior to imaging using a non-magnetic strapping mechanism, for example, a velcro strap or similar material/mechanism. The surfaces of the appendage cushions 70 may be shaped in a conformal nature to that of the patient's body. This shape provides for a more stable configuration so that there is little to no movement of the appendage cushions 70 relative to the patient.

Further, the upper surfaces of the appendage cushions 70 may be sloped downward in the direction towards the patient. This shape allows the arms, when in a relaxed state, to rest in the corner of the torso and the upper surfaces of the appendage cushions 70 which minimizes movement of the patient's arms during imaging.

In a preferred embodiment, the phase artifact related to respiratory and cardiac motion may be minimized by combining the T1 weighted imaging sequence with respiratory or electrocardiographic gating. Gating has the disadvantage of increasing the scan time, particularly in patients with irregular rhythms. Compensation techniques in which the mapping of the image data in k-space is matched to the respiratory and or cardiac cycle may eliminate some phase artifact without significantly increasing the scan time.

When imaging regions of the body that move substantially with respiration (e.g., the abdominal aorta and renal arteries) it may be useful to acquire data while the patient is holding his or her breath. This may require shortening the duration of the image acquisition time to under one minute. If the patient cannot hold his breath for the entire period of image acquisition, than it may be useful to hold the breath during acquisition of image data corresponding to the center of k-space and breathing only during acquisition of data corresponding to the periphery of k-space.

To facilitate breath holding during acquisition of image data which is representative of the central portion of k-space (i.e., the central half of k-space) it may be advantageous to order or arrange k-space centrically or in a shifted fashion so that the center of k-space is acquired in the beginning of the scan. In this way, if the patient begins breath holding at the beginning of the scan, the breath holding will automatically coincide with the collection of image data which is representative of the center of k-space. It may, however, be necessary to have a series of radio frequency pulses precede the center of k-space so that the background tissues reach their equilibrium degree of saturation. A few seconds of radio frequency pulses are sufficient in most cases for the tissues to reach dynamic equilibrium.

When imaging regions of the body that do not move substantially with respiration (e.g., femoral arteries) it may not be necessary to acquire data while the patient is holding his or her breath. Under these circumstances, the patient may begin breath holding for collection of image data of the image volume including the abdominal arteries (i.e., the first location 22). After collection of image data of the abdominal arteries, the platform is re-positioned at the next location (i.e., the second location 26) which includes regions of the body that do not move substantially with respiration. As such, the patient may breath for that and subsequent acquisitions.

With reference to FIGS. 2A–D, in one embodiment, the operator moves the platform 16 on platform table 18. Using handle 36, the operator may move the platform to various locations, for example the first, second, and third locations 22, 26, and 30, respectively. In one embodiment, to facilitate accurate and repeatable positioning of the platform 16, the interface of the platform 16 and platform table 18 may include a system of detents or slots. Under these circumstances, once the operator moves the platform 16 to a given location (e.g., location 26), the platform 16 is "pulled" into that location by the detent or slot by the momentum of the platform 16 and the shape of the platform-table interface. The operator may then move the platform 16 using handle 36 to the next location by overcoming the forces created by the detent or slot mechanism.

In another embodiment, an interlocking mechanism at the interface of the platform 16 and table 18 may be engaged such that relative movement is prevented until the interlocking mechanism is disengaged. The operator may disengage the interlocking mechanism by rotating or squeezing the handle 36. Once disengaged, the platform 16 may be moved to the next location.

Thus, the detent or slot system provides for consistent and accurate placement of the platform 16 at a given location while the interlocking mechanism provides for secure placement of the platform 16 until released.

Figure 7:
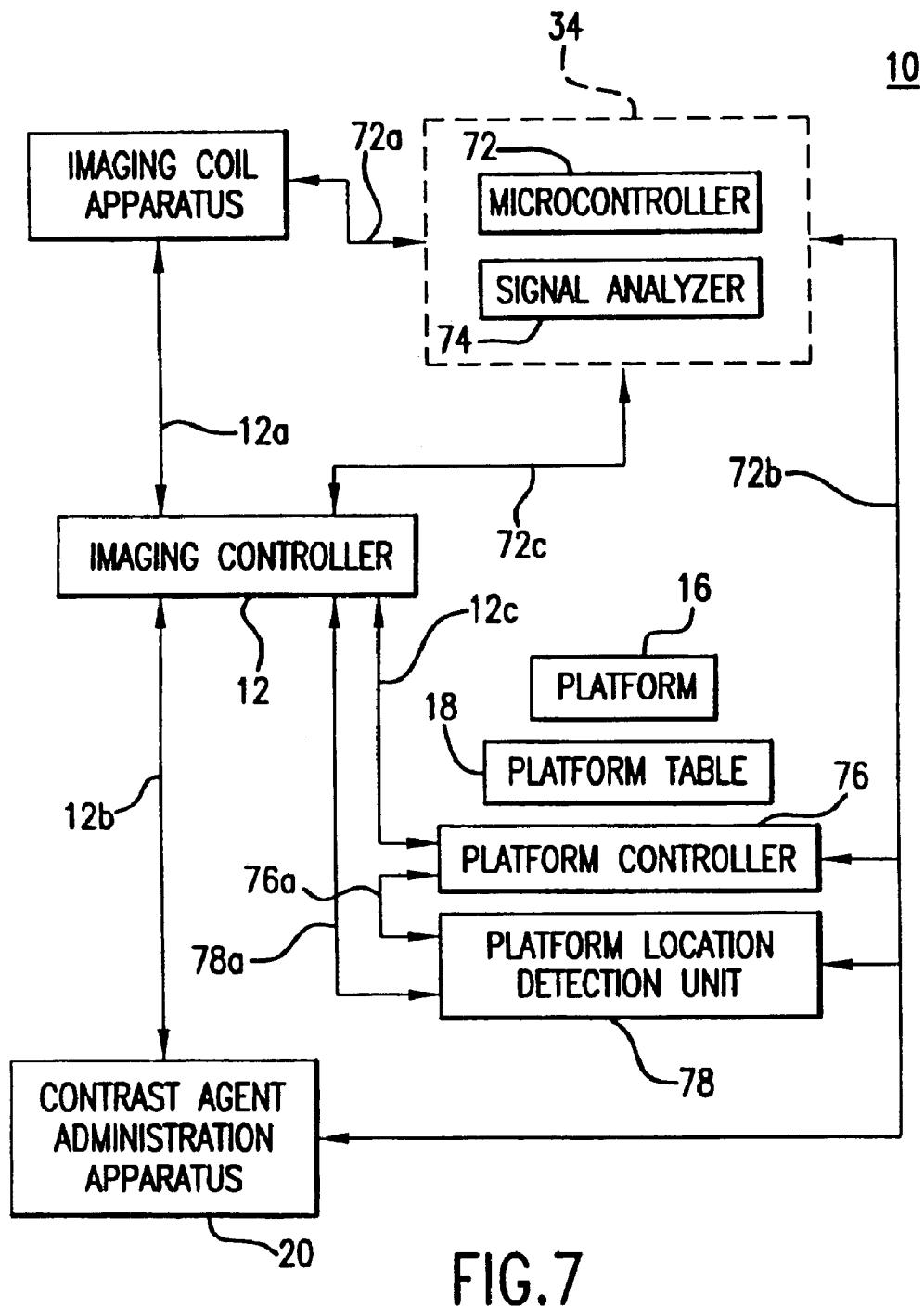
FIG. 7 is a block diagram representation of another embodiment of the magnetic resonance imaging system according to the present invention including a detailed block diagram representation of one embodiment of the detection system.

With reference to FIG. 7, in another embodiment of the present invention, the magnetic resonance imaging system 10 may further include a platform controller 76 and a platform location detection unit 78. In this embodiment, the platform controller 76 controls the movement and, as a result, the location of the platform 16; this, in turn, defines a corresponding image volume. The platform controller 76 may be mechanically coupled to the platform 16 to implement positioning and re-positioning of the platform 16.

In one embodiment, the platform controller 76 may position the platform 16 at any of an infinite number of locations on the platform table 18. Under these circumstances, the operator may tailor an imaging sequence according to the patient based on, for example, the size of the patient, location of the arteries to be imaged and the extent of the arterial system to be imaged. Stated differently, the operator may individualize a magnetic resonance arteriographic imaging sequence by programming a number of data acquisitions at different locations based on the specific patient. This may be accomplished by programming the image controller 12 and/or the platform controller 76. The platform controller 76, in response to that program, controls the location of the platform 16 for the entire imaging sequence. Since the platform controller 76 may repeatably and precisely position the platform in a given location, the operator has considerable flexibility in programming the overall imaging sequence.

In another embodiment, the platform controller 76 may situate the platform 16 into a number of discrete locations on the platform table 18. Here, the platform controller 76 positions and repositions the platform 16 among a given number of discrete locations during an imaging sequence. These pre-defined locations are the same regardless of the patient. In this embodiment, although the sequence of the image acquisition remains flexible, the locations are not. This, however, offers the operator the advantage of being able to repeatably and precisely position the platform 16 in a given location with a high degree of confidence. This ability to return to the exact same location facilitates use of digital subtraction magnetic resonance arteriography.

The platform controller 76 may be an electrical or pneumatic type mechanism. The type of controller may be dictated somewhat by the environment in which the controller is to be implemented in. For example, if the controller 76 is to be located in the magnetic resonance imaging suite and near the imaging coil apparatus 14, then a pneumatic type controller (a shaft coupled to the platform 16; the shaft being driven by compressed air) may be more suitable. However, if the controller 76 is to be located outside the suite or far from the coil apparatus 14, then an electrical type controller (e.g., shaft, gears or pulley system coupled to the platform 16; the shaft, gears or pulley system are driven by a motor) may be acceptable.

To insure very accurate and secure placement of the platform 16, the interface of the platform 16 and platform table 18 may include a series of detents or slots at that interface. Under these circumstances, once the platform controller 76 moves the platform 16 to a given, discrete location, the platform 16 is "pulled" or "forced" into that location by alignment of the platform 16 and the shape of the platform-table interface. Once in the detent or slot, an interlocking mechanism (not illustrated) may then engage the platform 16 and table 18 in order to prevent relative movement between the platform 16 and table 18 until the interlocking mechanism is disengaged. The detent or slot system (not illustrated) provides consistently accurate placement of the platform 16. The interlocking mechanism provides for secure placement of the platform 16 until released.

To further enhance the reliability and precision of platform placement as well as enhance automation of the system 10, a platform location detection unit 78 may be employed to provide position data of the platform 16. In one embodiment, the platform location detection unit 78 provides the system 10 with continuous, real-time information on the position of the platform 16. In another embodiment, the platform location detection unit 78 provides information as to which discrete location the platform 16 is positioned, if any.

In those embodiments where the platform 16 may be positioned in any location along table 18 (i.e., an infinite number of positions), it may be useful in programming the system 10 to have continuous, real-time information of the location of the platform 16. Here, the location detection unit 78 may provide feedback to the image controller 12 on the current location of the platform 16. With such continuous, real-time information, the image controller 12 may more precisely locate the platform 16 at a desired location. This will facilitate coordinating the collection of image data of a plurality of image volumes at a corresponding plurality of locations and the overlap of those volumes.

In those embodiments where the platform 16 may be positioned in a discrete set of locations, the platform location detection unit 78 may provide the system 10 with information relating to which discrete location currently occupied by the platform 16, if any. In this embodiment, the location detection unit 78 may handshake with the imaging controller 12 and/or the detection system 34 to indicate that the platform 16 has departed a given location (e.g., location 22) and has arrived at the next location (e.g., location 26 or 30).

It should be noted that other type platform location detection unit 78 may be employed. For example, not only may the platform location detection unit 78 provide continuous, real-time data representative of the location of the platform 16, but the platform location detection unit 78 may also provide information as to whether the platform 16 is at a specific, discrete location.

The system 10 of FIG. 7 may also enhance the rate of data acquisition (which is particularly important or useful while the imaging controller 12 is collecting central k-space data during the arterial phase of contrast enhancement) by alleviating the need for the operator to monitor the location of the platform 16, determine that the platform 16 is properly located, and initiate the next acquisition of image data. The decision as to whether to initiate data collection may be made by the imaging controller 12 when it either senses from or is informed by information provided by the platform location detection unit 78.

Moreover, in this embodiment, the platform location detection unit 78 allows for a more fully automated magnetic resonance imaging system 10. For example, in operation, upon collecting a particular set of image data at a given location (e.g., the central portion of k-space data and/or the periphery of k-space data), the imaging controller 12 may instruct the platform controller 76 to move the platform 16 to the next location. In response, the platform controller 76 moves the platform 16 to that location whereby the location detection unit 78 informs the controller 12 that the platform 16 is at the next location. In response, the controller 12 initiates collection of image data at that location.

In one embodiment, the location detection unit 78 is comprised of sensors (optical, electrical or mechanical type) at the discrete locations. These sensors provide the imaging controller 12 with information as to whether the platform 16 is at the location or not. Sensor may also be located at locations other than the locations fixed for imaging. It should be noted that, in this embodiment, the imaging controller 12 may maintain a position log within memory of the locations at which the platform 16 has been and should go. This position log may be built at the time the operator programs the imaging sequence of the patient.

Alternatively, the location detection unit 78 may be comprised of, for example, an optical encoder which provides data in the form of the absolute or relative position of the platform 16. The imaging controller 12 or location detection unit 78 may interpret that information and responsively instruct the platform controller 78 to move the platform 16.

It should be noted that the platform location detection unit 78 may be integrated within the platform controller 76. For example, the platform controller 76 may include a shaft, coupled to a pneumatic source, for moving the platform 16. The location detection unit 78 may be optically or electrically coupled to the shaft to measure or sense the relative movement of the shaft or the absolute position of the shaft. The location detection unit 78 may then provide that information to the imaging controller 12 which, in response, may instruct the platform controller 76 accordingly.

As will be appreciated by those skilled in the art, numerous other techniques and systems may be employed to not only control movement of the platform 16 but also determine the position of the platform 16. Those techniques and systems will be readily apparent by those skilled in the art of, for example, in control systems, from the aforementioned.

Image data which is representative of the center of k-space may be acquired using a number of different techniques and system. In one embodiment, with reference to FIGS. 2A–C, the operator may collect image data which is representative of the center of k-space for each of the image volumes by manually moving the platform 16 between the locations (e.g., first, second, and third locations 22, 26, and 30, respectively) of a imaging sequence. For example, when the platform 16 is located at a given location (e.g., the first location 22), the operator may initiate data acquisition of the central portion of k-space when the concentration of contrast in the artery(ies) is substantially greater than the concentration of contrast in veins and background tissue adjacent to the artery. After collecting image data at that location, the operator may move the platform 16 to the next location (e.g., the second location 26). In this embodiment, the operator manually moves the platform 16 between the various locations.

In another embodiment, the operator may program image data acquisition and, as such, the magnetic resonance arteriographic imaging sequence. In this regard, the operator may program the imaging controller 12 and/or the platform controller 76 to collect image data at a number of different locations. The system and technique of this embodiment provides the operator with considerable flexibility in individualizing or tailoring the overall imaging sequence to best suite the situation (e.g., the size and health of the patient, arteries to be imaged and the extent of the arterial system to be imaged).

In particular, since the platform controller 76 may repeatably and precisely position the platform 16 in a given location, the operator may individualize or tailor the imaging sequence according to the patient. Here, the operator may program the platform controller 76 to position the platform 16 at specific locations by choosing a size of the field of view, a desired amount of overlap between image volumes, and rate of data collection. It should be noted that a determination of the size of the field of view may be based on which size is best suited for the physical characteristics of the patient in addition to the physical and electrical characteristics of the imaging system 10.

In this embodiment, the platform controller 76, in response to instructions from the imaging controller 12, moves the platform 16 between the selected or programmed locations. In operation, upon collecting at least image data which is representative of the center of k-space while the concentration of contrast agent in the artery(ies) in the imaging volume is substantially greater than that in the veins or background tissue adjacent to the artery(ies), the imaging controller 12 instructs the platform controller 76 to move the platform 16 to the next location. When the platform 16 is at the next location, the imaging controller 12 collects image data including data which is representative of the center of k-space while the concentration of contrast agent in the artery(ies) in the imaging volume is substantially greater than that in the veins or background tissue adjacent to the artery(ies). This continues until image data for all of the image volumes is collected.

In another embodiment, the detection system 34, in conjunction with the imaging controller 12 and imaging coil apparatus 14, monitors and detects the relative concentration of the contrast agent in the region of interest by comparing the response of a region of interest before the administration of magnetic resonance contrast agent to the patient to the response of the region of interest during and/or after administration of the contrast agent. When a characteristic change in the response to the magnetic resonance pulse is measured by the detection system 34, the imaging system 10 begins collecting image data which is representative of the center of k-space.

As mentioned above and discussed in detail in U.S. Pat. No. 5,590,564, some of which is reproduced below, the detection system 34 detects the concentration of contrast agent in the region of interest. More specifically, the detection system 34 detects the "arrival" of contrast in the region of interest and/or detects the concentration of contrast therein. The detection system 34 may also be used to precisely synchronize the collection of a predetermined portion of image data (e.g., center of k-space) by the imaging system 10 with the arterial phase of contrast enhancement of the region of interest (artery and background tissue in the region of interest).

In operation, prior to administration of contrast agent to the patient and before initiation of the imaging sequence, the detection system 34 initially measures the response from the region of interest to a series of pulses from the imaging system 10. Here, the detection system 34 acquires a response from the region of interest before administration of contrast agent. This response may be described as a base line or pre-contrast response.

After the base line or pre-contrast response is measured, the contrast agent may be administered to the patient. The detection system 34 may then measure the response from the region of interest to a series of magnetic resonance pulses from the imaging system 10. The detection system 34 or the operator may evaluate the response from the region of interest to determine a characteristic change in the response from the region of interest. This characteristic response may indicate the arrival of contrast in the region of interest or the onset of the arterial phase of contrast enhancement.

The subsequent operations of the detection system 34 depend somewhat on the parameters of injection rate of the contrast administration apparatus 20 and the data collection techniques and configuration of the imaging system 10. In those instances where the injection of the contrast agent is of a bolus type (i.e., rapid injection rate), the characteristic change in the response to the magnetic resonance pulses may indicate that the region of interest is in or is "entering" the arterial phase of the magnetic resonance contrast enhancement. Under this circumstance, the detection system 34 instructs the imaging system 10 to initiate an imaging sequence at the first location 22. The imaging system 10, immediately or shortly thereafter, collects the predetermined image data (e.g., center of k-space) of the first imaging volume 24 when the platform 16 is at the first location 22.

It may be useful to have a short delay between detecting the arrival of contrast in the arteries of interest and beginning collecting data representative of the center of k-space. This delay may allow the contrast to reach all of the arteries throughout a given imaging volume (region of interest). However, in those instances where there are several locations at which to collect image data, there may not be sufficient time to collect image data which is representative of the center of k-space during the arterial enhancement phase at all of the locations; as such, the system 10 may initiate collection of image data without a short delay after detecting the arrival of contrast in the arteries of interest.

Where a bolus injection is employed, the magnetic resonance imaging pulse sequence may be arranged such that the central portion of k-space data is collected in the beginning or near the beginning of the sequence. The periphery of k-space may be collected before or after collecting the central portion. This process may be employed at each location. That is, for each image volume, the periphery of the central portion of k-space may be collected before or after collecting the central portion of k-space. Under this circumstance, the detection system 34 provides more precise synchronization between the arterial phase of contrast enhancement and the collection of image data which is representative of the center of k-space.

In another embodiment, the detection system 34 may detect the arrival (or a predetermined concentration of contrast agent) in a field of view in the aorta. In response, the imaging controller 12 may initiate imaging of the abdominal aorta reverse centrically; that is collecting the center of k-space towards the end of the image scan. After the platform 16 is re-positioned at the second location 26, the image controller 12 may collect the image data centrically; that is collecting image data which is representative of the center of k-space first. Under these circumstances, the centers of k-space for the first and second sequences (first and second image volumes 24 and 28) are close in temporal proximity to one another.

It should be noted that the detection system 34 may be employed at each location (22, 26 and 30) of a given sequence. That is, the detection system 34 may be used to detect the onset of the arterial phase of contrast enhancement at the first location 22; then after collecting the central portion of k-space, the is platform 16 may be positioned at the second location 26; the detection system 34 may then detect the onset of the arterial phase of contrast enhancement in the arteries in the second image volume 28. The detection system 34 may also be employed in a similar manner when the platform 16 is positioned at the third location 30.

Where the magnetic resonance pulse sequence collects data which is representative of the center of k-space in the middle of the scan (a conventional type scan), the detection system 34 may be employed to determine an "adjustment" of the infusion rate of the contrast agent by the contrast agent administration apparatus 20 so that a period of maximum or substantially elevated concentration of contrast agent in a given region of interest is correlated to the collection of image data which is representative of the center of k-space (i.e., mapping of k-space). As noted in U.S. Pat. No. 5,553,619, the time between contrast injection and a maximum or substantially elevated contrast concentration in the artery of interest may vary according to a number of factors including the location of the artery of interest, the size of the artery of interest, the physical condition of the patient, and the time delay due to the configuration of the contrast agent administration apparatus 20. In this embodiment, the detection system 34 may be employed to automatically adjust the rate of administration of the administration apparatus 20 so that the imaging sequence collects a sufficient amount of data which is representative of k-space during the arterial phase of the enhancement of the region of interest before the platform is re-positioned at another location.

In this embodiment, the detection system 34 monitors the response of the region of interest to series of magnetic resonance detection pulses. When the detection system 34 determines that the contrast has "entered" the region of interest, the detection system 34 may adjust the rate of injection of the contrast agent to alter the timing of the arterial phase of contrast enhancement in the arteries within the current or subsequent image volumes.

The detection system 34 may calculate an adjustment to the rate of infusion based on several factors including the circulation time delay of the contrast agent, the timing of the mapping of k-space, and the current and future rates of infusion. The detection system 34 may then increase or decrease the rate of injection by the administration apparatus 20 accordingly to provide sufficient or maximum overlap between the mapping of k-space and the arterial phase of contrast enhancement in the arteries within the current or subsequent image volumes.

FIG. 7 illustrates one embodiment of the detection system 34 of the present invention. In this embodiment, the detection system 34 includes a microcontroller 72 and a signal analyzer 74 (e.g., an oscilloscope). In one embodiment, the microcontroller 72 includes an operator interface which allows the operator to observe the response measured by the signal analyzer 74. In this embodiment, the microcontroller 72 facilitates the operator's observation and analysis of response signals including assessing the concentration of contrast in the region of interest. The microcontroller 72 may include a visual and/or audible indicator to indicate the onset of the arterial phase of contrast enhancement or to indicate the concentration of contrast agent in the artery of interest. Such a configuration would facilitate synchronization between the collection of image data which is representative of the center of k-space with the arterial phase of contrast enhancement.

It should be noted that the operator may observe the signal measured by the signal analyzer 74 in addition to or in lieu of the operator interface of the microcontroller 72. Under this circumstance, the microcontroller 72 may be unnecessary.

In another embodiment, the microcontroller 72 controls the rate of infusion by the contrast agent administration apparatus 20 (e.g., a mechanical pump, Life Care 5000 and/or the size of the orifice of the fluid flow restrictor for a mechanical infusion apparatus, e.g., the apparatus illustrated in FIGS. 5A and 5B of U.S. Pat. No. 5,590,654). Similar to the control of the imaging system 10, the microcontroller 72 (which is appropriately programmed) may adjust the rate of infusion to correlate the collection of image data which is representative of the center of k-space with a maximum, elevated, or substantially elevated concentration of contrast agent in the region of interest. The microcontroller 72 may adjust the rate of injection via controlling the infusion adjustment mechanism on the administration apparatus 20. The microcontroller 72 couples to the administration apparatus 20 via electrical, optical, or pneumatic coupling mechanism 72b.

As mentioned above, the detection system 34 may compute an adjustment to the infusion parameters or sequence of administration apparatus 20 based on several factors including the circulation time delay, the relative timing of the mapping of k-space, and pre-programmed rate of infusion. The detection system 34 may then increase or decrease the rate of injection by the infusion device 12, via the infusion adjustment mechanism, to provide a period of arterial phase of contrast enhancement which extends during the collection of image data which is representative of the center of k-space.

It should be noted that in the foregoing embodiments, the periphery of k-space for each of the image volumes may be collected before or after collecting image data which is representative of the center of k-space. In those instances where the periphery of k-space is collected before collecting image data which is representative of the center of k-space, the platform 16 may be positioned at each of the locations (e.g., the first, second and third locations, 22, 26, and 30, respectively) before administration of the contrast agent. These locations will be the same as those which the platform will be positioned when collecting image data which is representative of the center of k-space. This data, along with the data representative of the center of k-space, may be used to generate the final images.

In those instances where the periphery of k-space for each of the image volumes is collected after collecting image data which is representative of the center of k-space, the periphery of k-space may be collected immediately after collecting the center of k-space and before the platform is moved to the next location or after the center of k-space is collected for all of the locations. In those situations where the arterial phase of contrast enhancement is short, it may be important to rapidly collect image data representative of the center of k-space; this may require that the periphery of k-space data be collected for each of the image volumes after collecting central k-space data for each of those volumes.

In a preferred embodiment, the imaging system 10 employs fast three dimensional (3-D) magnetic resonance imaging sequences to collect the image data of the image volumes. These sequences may include a 3-D gradient echo pulse sequence and, in a preferred embodiment, a 3-D spoiled gradient echo pulse sequence. The parameters of these sequences, which are discussed in detail below, are chosen to optimize the spatial coverage relative to the time necessary to collect the image data of the image volumes.

Under those circumstances, the TR is designed to be as short as possible without producing saturation effects in order to reduce imaging time. In a preferred embodiment, the TR is less than or equal to 30 millisecond and more preferably is less than 10 milliseconds. In an even more preferred embodiment, TR is less than 5 milliseconds.

TE is selected as short as possible in order to reduce data acquisition time. Where the imaging coil apparatus 14 is a 1.5 Tesla superconducting magnet (e.g., an Horizon system from General Electric Medical Systems, Milwaukee, Wis.), in a preferred embodiment, TE is less than or equal to 7 milliseconds. In a more preferred embodiment, TE is less than 3 milliseconds and in an even more preferred embodiment, TE is about 2.1 msec.

The flip angle may be optimized according to Ernst equation or may be optimized empirically. In a preferred embodiment, the flip angle may be between about 30° to about 90°. Under the circumstances where the TR is set between 5 to 7 milliseconds and the infusion rate of the contrast agent is between about 0.5 to about 1 cc/sec, a flip angle of between 35° to 45° is preferred.

The resolution of the image is governed primarily by the matrix size, field of view and number of slices within the 3D imaging volume. Optimal imaging within a sufficiently short time-period results in a trade-off between these competing parameters. These parameters may be selected as follows.

The matrix size is optimized to produce maximal resolution within a reasonable imaging time. At present 256 (frequency)×128–192 (phase) although other values may also be appropriate.

There is a trade-off between increasing the field of view to the maximum allowed for the imaging system 10, the number of locations necessary to image the arteries and the need for adequate anatomical resolution. For example, where the field of view is 48 centimeters, two locations are necessary to image a patient from the abdominal aorta to the plantar arteries. Although superior spatial resolution will be achieved by using a smaller field-of-view, this may necessitate the use a larger number of imaging locations in order to image the desired portion of the arterial system. In general the largest field of view will be preferred. However, some imaging systems have artifact at the edges of the imaging volume when the largest field of view is used. Under this circumstance, it may be preferred to use a smaller field of view that excludes artifactual regions.

An asymmetric field-of-view in the phase-encode direction (for example, three quarter of the field of view) can be used to shorten imaging time by reducing the number of phase-encode steps necessary at each location. Alternatively, an asymmetric field of view may be used without reducing the number of phase-encode steps to give increased resolution without the time penalty inherent in increasing the number of phase-encode steps.

Where the vasculature from the supra-renal aorta to the level of the foot arteries is desired, the imaging volume must be of sufficient thickness to account for variations in height of the arteries to be imaged. The course or path of the arteries do not follow a straight line in the sagittal plane from aorta to foot Rather, the height of those arteries relative to the top surface of the platform 16 (i.e., the distance of the arteries above the platform 16) vary considerably. As such, the imaging volume should be sufficiently thick to include all of the arteries at the expected heights above the platform 16.

It should be noted that as discussed above, the variations of the vertical locations/path of the arteries may be reduced by using a system and technique of raising certain limbs, e.g., the legs and feet. By adjusting the height of the limbs, the arteries in those limbs will have less of a vertical deviation from arteries in the torso.

The bandwidth may be optimized to produce maximum contrast and signal-to-noise within as short a time period as possible. Once again, there is a trade-off between utilizing a narrower bandwidth which tends to improve signal-to-noise versus a wider bandwidth which tends to generate lower signal-to-noise images but which is acquired in a shorter time-period. In a preferred embodiment, the bandwidth is typically 16 kHz to 32 KHz, although another bandwidth may be appropriate.

As for the number of excitations, typically one excitation for most gadolinium-enhanced magnetic resonance arteriography at present. However, partial Fourier imaging (partial NEX) may be preferable in order to reduce imaging time.

As for the amount of contrast agent to be employed, the dose of contrast agent may be tailored to the patient depending upon such variables as the patient's weight, estimated circulation time, and relaxivity of the contrast agent. Where the contrast agent is a gadolinium chelate, a dose of from about 20 mL to about 60 mL (about 7.5 mMol to about 30 mMol) may be adequate.

In order to image the different locations in sufficiently rapid succession to "follow" the contrast agent bolus down the torso and legs, it may be necessary to use special techniques to get the fastest possible scan time. These techniques may include partial Fourier imaging (partial NEX), high speed gradients, echo planar pulse sequences, keyhole imaging, partial field-of-view (rectangular field-of-view), zero padding, among others.

One additional approach which was discussed above, was to collect central k-space data dynamically at each location when the arterial gadolinium concentration is high and following the gadolinium bolus from the abdomen down the leg. This way of collecting central k-space data at each location will match the moment of maximum arterial gadolinium concentration at all locations. Then, after central k-space data is collected at all locations, one can go back to each location to collect the remainder of k-space data, the peripheral k-space data. Alternatively, peripheral k-space data could be collected prior to scanning or it could be an average or weighted average of data collected pre and post-contrast.

It should be noted that with the improvements of technology, it is expected that as the capability of acquiring a larger number of slices in a relatively reasonable time frame will increase. This may render several of these modifications or considerations obsolete or moot.

In one preferred embodiment, additional contrast is obtained by digitally subtracting image data acquired before administration of the contrast agent from the dynamic acquisition. Here, a pre-contrast set of images may be acquired at each image location. The purpose may be two-fold: (1) to determine appropriate placement of the imaging volume; and (2) to provide a "mask" for subtraction from the post-contrast images to improve depiction of the vessels by subtracting background tissues in some cases. This will require accurate repositioning of the table for each set of post-contrast images to the exact location of the pre-contrast images to avoid errors in background subtraction. Thus, the positioning of the platform 16 should be highly repeatable and accurate when locating the platform 16 for pre-contrast data acquisition as well as when locating the platform 16 during and/or post-contrast agent administration data acquisition. As such, when implementing this embodiment, it may be useful to use the detent or slot mechanism described above to ensure that the platform 16 returns to the same location during and/or post-contrast agent administration as pre-contrast imaging.

In another preferred embodiment, additional contrast is obtained by digitally subtracting image data collected during the equilibrium phase of contrast enhancement from the dynamic acquisition. As with the previous embodiment, the positioning of the platform 16 should be highly repeatable and accurate when locating the platform 16 for pre-contrast data acquisition as well as during and/or post-contrast agent administration data acquisition. As indicated above, the detent or slot mechanism described above facilitates repeatable and precise discrete placement of the platform 16 thereby ensuring that the platform 16 returns to the same location when collecting image data of the image volumes during/post-contrast agent administration when compared to pre-contrast image data acquisition.

Using a 1.5 Tesla, imaging system manufactured by General Electric Medical Systems, five patients were imaged successfully during the arterial phase of a single gadolinium contrast bolus covering arteries from abdominal aorta to distal calf. To do this on the General Electric scanner, the existing platform was disengaged from its chain driven movement mechanism so that it could be moved more rapidly by hand from location to location. Each patient was carefully positioned on the platform with the legs and ankles elevated so that they were of similar height above the platform as the aorta. Straps were used to hold the legs together and to prevent motion of the legs relative to the table.

A 3D spoiled gradient echo pulse sequence was prescribed from a sagittal localizer. The 3D spoiled gradient echo pulse sequence utilized the following parameters: TR=6.9 msec, TE=2.1 msec (fractional echo), flip angle=45 degrees, slice thickness=2.8 mm, field-of-view=36 cm, matrix=256×160, 36 slices with interpolation using zero padding to reconstruct a total of 72 slices at 1.4 mm intervals. Using a partial Fourier acquisition (0.5 NEX) it was possible to obtain an entire 3D volume of image data in 27 seconds. The multi-phase option was selected so that this 3D volume of image data could be repeatedly acquired with only a few second delay in between acquisitions. During these delays the table could be moved to the next location.

In order to slow down the blood flow in two patients, tourniquets were applied to the calves and thighs. The gadolinium dose was 21 mMol (42 cc). It was infused at a rate of about 1–2 cc per second by hand using IV tubing with two ports to allow simultaneous attachment of gadolinium and saline flush syringes. (See, FIG. 5B). The gadolinium infusion was immediately followed with a saline flush. Optimal arterial phase imaging was achieved by using a pulse sequence that detected the arrival of the gadolinium in the aorta and automatically initiated acquisition of 3D spoiled gradient echo imaging beginning with the central k-space data. A short delay (i.e., 5 seconds) was provided between detection of the leading edge of the bolus and initiation of data acquisition to allow time for the patient to take in a breathe and then suspend breathing.

Following completion of the first 3D volume of imaging (abdomen and pelvis), the table was rapidly moved by hand to the second imaging volume (thighs) and acquisition of another 3D image data set was initiated. The time to move the table was less than 3 seconds. After completion of the second image volume, the table was repositioned again by hand to collect the third volume of image data. After all the data was acquired, it was analyzed and reformatted on a computer workstation.

Various preferred embodiments of the present invention have been described. It is understood, however, that changes, modifications and permutations can be made without departing from the true scope and spirit of the present invention as defined by the following claims, which are to be interpreted in view of the foregoing.

What is claimed is:

1. A method of imaging arteries in a human patient using a magnetic resonance imaging system and a magnetic resonance contrast agent, wherein the arteries include a first artery which is located in a first image volume, a second artery which is located in a second image volume and a third artery which is located in a third image volume, the method comprising:

injecting the human patient with the magnetic resonance contrast agent via substantially one injection;

collecting magnetic resonance image data of the first image volume, wherein at least a portion of the image data of the first image volume is collected during an arterial phase of contrast enhancement of the first artery and wherein the first artery is in the abdomen or the pelvis of the human patient;

collecting magnetic resonance image data of the second image volume, wherein at least a portion of the image data of the second image volume is collected during an arterial phase of contrast enhancement of the second artery and wherein the second artery is in a leg of the human patient; and collecting magnetic resonance image data of the third image volume, wherein at least a portion of the image data of the third image volume is collected during an arterial phase of contrast enhancement of the third artery and wherein the third artery is in a foot of the human patient.

2. The method of claim 1 further including constructing an image of the first artery using the image data of the first image volume and an image of the second artery using the image data of the second image volume.

3. The method of claim 2 further including combining the image of the first artery with the image of the second artery in a mosaic manner.

4. The method of claim 1 further including applying a tourniquet to the patient to reduce blood flow in a calf or a thigh of the human patient.

5. The method of claim 1 wherein collecting the magnetic resonance image data of the second image volume includes collecting image data which is representative of the center of k-space substantially at a beginning of a second imaging sequence.

6. The method of claim 1 further including administering the magnetic resonance contrast agent to the patient over a substantial portion of the period of collection of the image data of the first image volume.

7. A method of imaging arteries in a patient using a magnetic resonance imaging system, wherein the arteries include a first artery which is located in a first image volume and a second artery which is located in a second image volume, the method comprising:

injecting a magnetic resonance contrast agent of substantially one injection into the patient, wherein the magnetic resonance contrast agent is injected using, a coiled conduit having a first end, a second end and an inner diameter;

a multiport adapter connected to the first end of the coiled conduit, the multiport adapter having at least two input ports wherein each input port includes a one way valve; and a locking mechanism coupled to the second end of the coiled conduit wherein the locking mechanism is capable of securing the coiled conduit to a catheter in the patient;

collecting magnetic resonance image data of the first image volume, wherein a substantially portion of the magnetic resonance image data of the first image volume is collected during an arterial phase of contrast enhancement of the first artery;

positioning the patient in a second location to define a second field of view which encompasses the second artery wherein the second artery is a femoral artery, a popliteal artery or a tibial artery of the patient; and collecting magnetic resonance image data of the second image volume, wherein a substantially portion of the magnetic resonance image data of the second image volume is collected during an arterial phase of contrast enhancement of the second artery.

8. The method of claim 7 further including constructing an image of the first artery using the magnetic resonance image data of the first image volume and an image of the second artery using the magnetic resonance image data of the second image volume.

9. The method of claim 8 further including combining the image of the first artery with the image of the second artery in a mosaic manner.

10. The method of claim 7 wherein collecting the magnetic resonance image data of the first image volume includes collecting image data which is representative of the center of k-space substantially at a beginning of a first imaging sequence.

11. The method of claim 7 wherein collecting the magnetic resonance image data of the second image volume includes collecting image data which is representative of the center of k-space substantially at a beginning of a second imaging sequence.

12. The method of claim 7 further including applying a tourniquet to the patient to reduce blood flow in a calf or a thigh of the patient.

13. A magnetic resonance imaging system for imaging arteries in a patient using an injected contrast agent of substantially one injection, wherein the arteries include a first artery which is located in a first image volume and a second artery which is located in a second image volume, the system comprises:

an injection apparatus including, a coiled conduit having a first end, a second end and an inner diameter;

a multiport adapter connected to the first end of the coiled conduit, the multiport adapter having at least two input ports wherein each input port includes a one way valve; and a locking mechanism coupled to the second end of the coiled conduit wherein the locking mechanism is capable of securing the coiled conduit to a catheter;

a platform to support the patient, the platform being moveable between a plurality of locations including a first location which defines a first field of view encompassing the first artery and a second location which defines a second field of view encompassing the second artery, wherein the first field of view and the second field of view are 48 cm or less; and magnetic resonance imaging unit to collect magnetic resonance image data of the first image volume during an arterial phase of contrast enhancement of the first artery and while the platform is positioned at the first location, and to collect magnetic resonance image data of the second image volume during an arterial phase of contrast enhancement of the second artery and while the platform is positioned at the second location.

14. The system of claim 13 wherein the magnetic resonance imaging unit constructs an image of the first artery using the magnetic resonance image data of the first image volume and an image of the second artery using the magnetic resonance image data of the second image volume.

15. The system of claim 13 wherein the coiled conduit is substantially transparent.

16. The system of claim 13 wherein the coiled conduit is flexible and is comprised of a plastic material having a hardness and wall thickness sufficient to prevent kinking.

17. The system of claim 13 wherein the multiport adapter includes a first input port and second input port, wherein the first input port is adapted to receive a syringe containing a magnetic resonance contrast agent and the second input port is adapted to receive a syringe containing a flush solution.

18. The system of claim 17 wherein the first input port extends in a first direction and the second input ports extends in a second direction such that an angle formed by the first and second input ports is greater than about 10 degrees and less than about 45 degrees.

19. The system of claim 18 wherein the wherein the angle formed by the first and second input ports is greater than about 30 degrees and less than about 40 degrees.

20. The system of claim 18 wherein the multiport adapter is a two port "Y" bifurcate.

21. The system of claim 13 wherein the inner diameter of the conduit is greater than about 0.04 inches and less than about 0.12 inches.

22. The system of claim 13 wherein the inner diameter of the conduit is greater than about 0.06 inches and less than about 0.10 inches.

23. The system of claim 13 wherein the inner diameter of the conduit is sufficiently large to provide minimum resistance to fluid flow and sufficiently small to provide minimum dead space.

24. The system of claim 13 wherein the thickness of the conduit is greater than about 0.02 inches and less than about 0.08 inches.

25. The system of claim 13 wherein the locking mechanism is a male luer locking mechanism having a male luer protector and a male luer swivel.

26. The system of claim 13 wherein the coiled conduit may be extended longer than 3 meters.

27. The system of claim 13 Wherein the coiled conduit has a hardness of about 80 on the Shore A Hardness scale.

28. The system of claim 13 wherein the magnetic resonance imaging unit collects the center of k-space of the second image volume substantially at a beginning of a first imaging sequence.

29. The system of claim 13 wherein the magnetic resonance imaging unit collects the center of k-space of the first image volume substantially in a middle of a first imaging sequence.

30. The system of claim 29 wherein the magnetic resonance imaging unit collects the center of k-space of the second image volume substantially in the middle of a second imaging sequence.

* * * * *